(12) United States Patent
Liu et al.

(10) Patent No.: US 8,551,447 B2
(45) Date of Patent: Oct. 8, 2013

(54) BIFUNCTIONAL COMPOUND WITH MONOSACCHARIDE AND N2S2 LIGAND, AND PREPARATION AND USE THEREOF

(75) Inventors: Show-Wen Liu, Changhua County (TW); Cheng-Hsien Lin, Taipei (TW); Yu Chang, Taipei (TW); Cheng-Fang Hsu, Miaoli County (TW); Tsyh-Lang Lin, Taoyuan County (TW)

(73) Assignee: Institute of Nuclear Energy Research Atomic Energy Council, Executive Yuan, Taoyuan County (TW)

( * ) Notice: Subject to any disclaimer, the term of this patent is extended or adjusted under 35 U.S.C. 154(b) by 307 days.

(21) Appl. No.: 13/087,664

(22) Filed: Apr. 15, 2011

(65) Prior Publication Data
US 2012/0009669 A1  Jan. 12, 2012

(51) Int. Cl.
*A61K 38/00* (2006.01)
(52) U.S. Cl.
USPC ....... 424/1.69; 424/1.37; 424/1.65; 424/1.73; 424/9.35
(58) Field of Classification Search
USPC ........ 424/1.37, 1.65, 1.69, 1.73, 9.35; 514/54
See application file for complete search history.

(56) References Cited

U.S. PATENT DOCUMENTS 6,019,958 A * 2/2000 Dean et al. ................... 424/1.69

OTHER PUBLICATIONS

K. Chryssou et al., Synthesis and structural characterization of the [2,9-dimethyl-4,7-diaza-2,9-decanedithiolato]oxorhenium(V) complex, Inorganica. Chemica. Act. 268, 169-175, 1998.*
Mitsuru Hashida et al., Hepatic targeting of drugs and proteins by chemical modification, Journal of Controlled Release 36, 99-107, 1995.*

* cited by examiner

*Primary Examiner* — Michael G Hartley
*Assistant Examiner* — Jagadishwar Samala
(74) *Attorney, Agent, or Firm* — WPAT, PC; Justin King

(57) ABSTRACT

A bifunctional compound with a monosaccharide and a $N_2S_2$ ligand, and more particularly, a bifunctional compound with a $N_2S_2$ ligand and aminohexylacetyl galactosamine (ah-Gal-$NAc_4$) is provided. A method for preparing the bifunctional compound with a monosaccharide and a $N_2S_2$ ligand is also provided, including activating a carboxyl group in an organic ligand, reacting the activated carboxyl group with a galactopyranoside through amidation, and then hydrolyzing. The bifunctional compound of the present invention is widely useful in nuclear medicine for preparation of liver imaging agents for assisting in correct diagnosis of diseases.

11 Claims, 24 Drawing Sheets

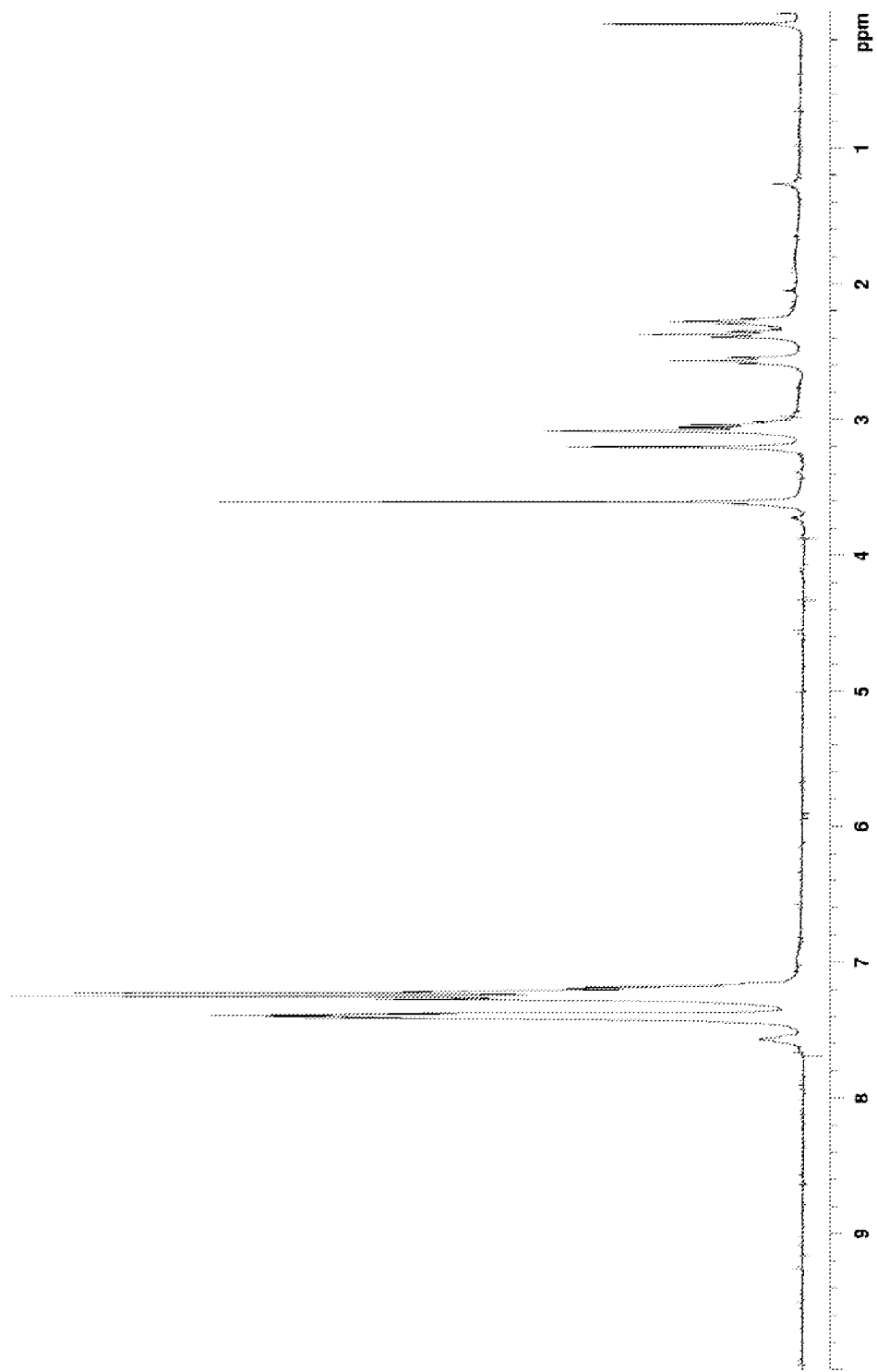

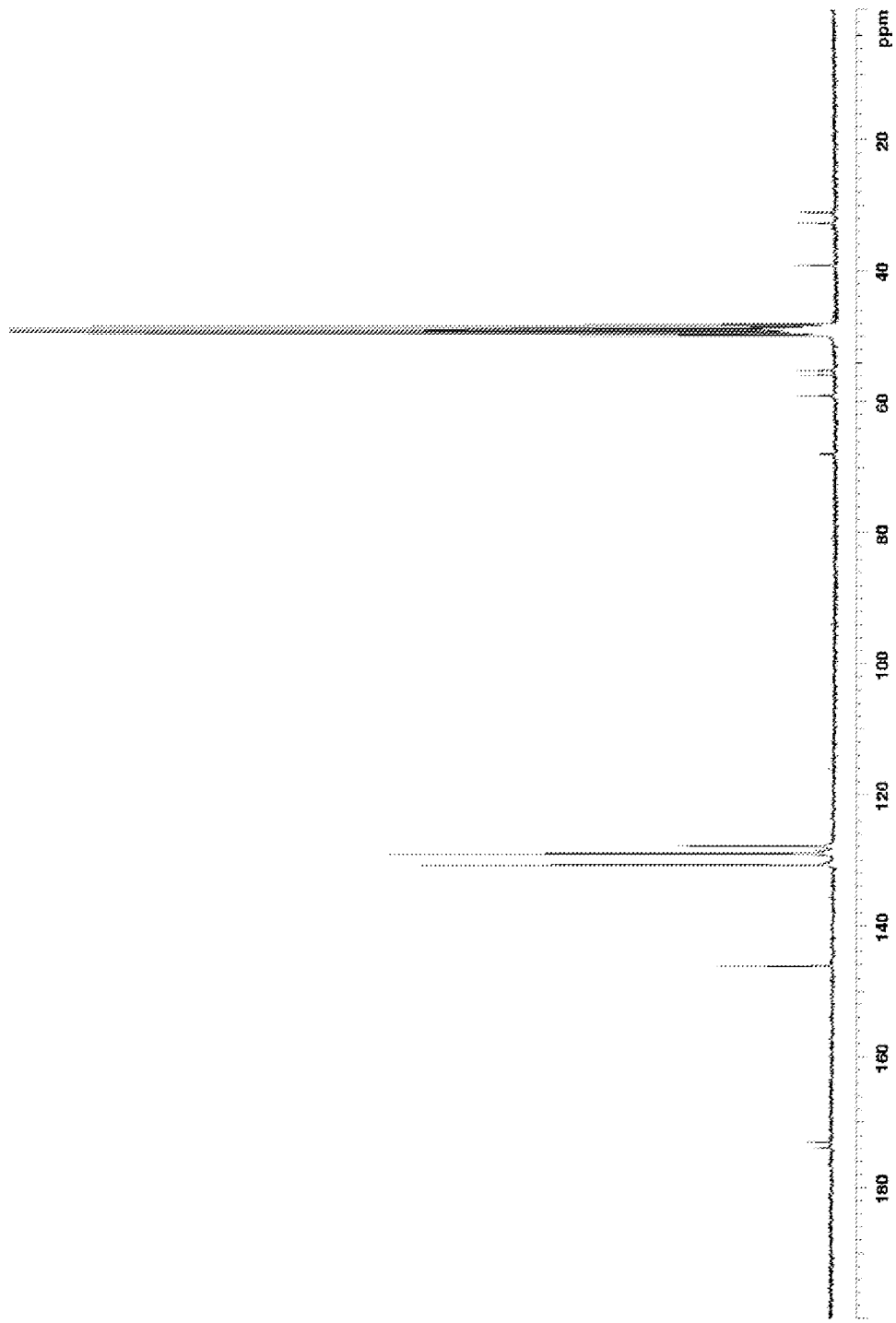

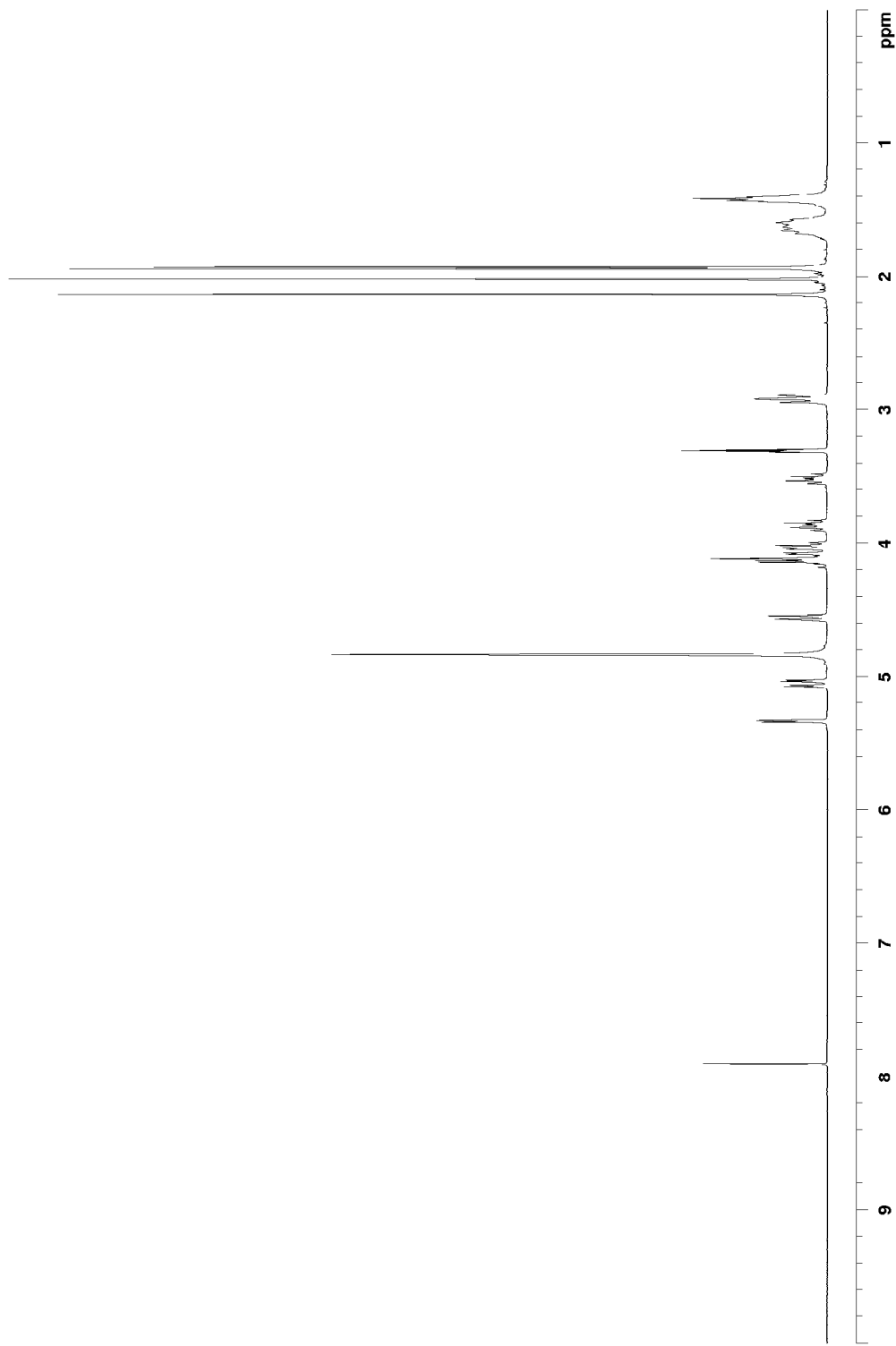

BIFUNCTIONAL COMPOUND WITH MONOSACCHARIDE AND N2S2 LIGAND, AND PREPARATION AND USE THEREOF

BACKGROUND OF THE INVENTION

1. Field of Invention

The present invention relates to a bifunctional compound with a monosaccharide and a $N_2S_2$ ligand, and preparation and use thereof, and more particularly to a bifunctional compound with aminohexyl N-acetylgalactosamine (ah-Gal-NAc).

2. Related Art

In studies on non-invasive detection of liver fibrosis, imaging in nuclear medicine with radio-labeled glycoprotein reflecting liver function is generally performed with liver asialoglycoprotein receptor (ASGPR), which is applied in test of residual liver function in a human.

ASGPR is a phagocytic receptor merely existing on surface of mammal liver cells, and can specifically identify sugar chains with a terminal galactosamine (Gal) or N-acetylgalactosamine (GalNAc). Hashida et al (Hashida M, Nishidawa M, Tadakura Y., J Controlled Release, 36(1):99, (1995)) concluded through comparison with experiments that, in view of reflection of liver function, SPECT imaging of liver ASGPR is significantly superior to other imaging means. ASGPR is high affinity to liver, and can be quickly absorbed by the liver. A number of ASGPR changes when lesions occur to the liver, and thus, a novel contrast medium for liver cell fibrosis in nuclear medicine can be developed based on this.

Currently, in studies on ASGPR contrast medium, a bifunctional compound is generally used, and Tc-99m is confirmed to be stably chelated in coordination bonding with a series of bifunctional ligands containing $N_2S_2$, to form a complex. A $N_2S_2$ ligand is bonded with Tc-99m in a five coordination manner, in which coordination binding occurs between Tc-99m and $N_2S_2$, thus forming a stable pyramid configuration. Types and structures of common $N_2S_2$ bifunctional chelating agents are as follows (Chryssou K, Inorganica Chimica Acta Vol. 268,169 (1998)).

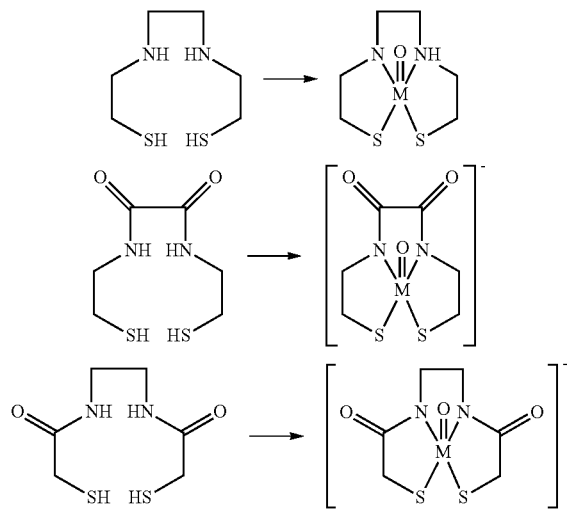

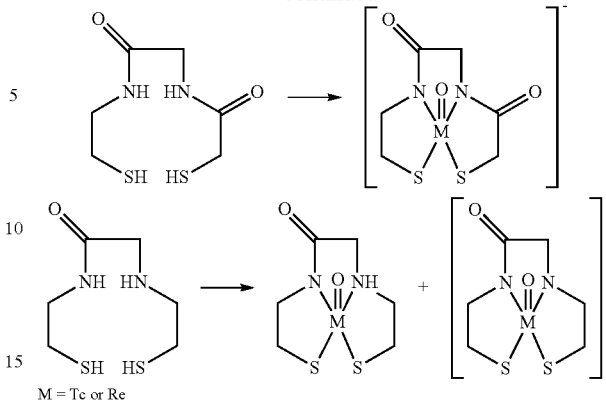

M = Tc or Re

It was suggested to use a radiopharmaceutical Tc-99m-DTPA-galactosyl-albumin (a liver asialoglycoprotein) as a contrast medium in nuclear medicine of liver asialoprotein receptor in imaging of liver function (Toyama H, Suzuki K, Naito A et al, Ann Nucl Med, 13, 155-160, (1999)). Although a general test agent can rapidly evaluate the liver function in vitro, how much function of the liver is left cannot be known. However, with Tc-99m-DTPA-galactosyl-albumin as a radiopharmaceutical, not only how many liver cells are alive, but also which regions still function can be known. Clinical significance of a contrast medium of liver asialoprotein in nuclear medicine lies in that, as transient hypoxia of liver cells is frequently caused after liver transplantation, it is necessary to determine how many liver cells are still alive with galactosyl-albumin-DTPA-Tc-99m after operation, so as to determine the success of the liver transplantation.

Presently, many researches on ligands that specifically bind to the liver cells are reported, and the ligands are widely used. For example, a research (Khorev O, Stokmaier D, Schwardt O, Cutting B, Ernst B. Trivalent, Bioorg Med Chem; 16:5216-5231. (2008)) indicates that synthesized ligands or peptides containing trivalent β-linked Gal or Gal-NAc branched saccharide structure have high affinity and specificity to ASGPR, and can be selectively endocytosed by HepG2 liver cell lines. Another research also verifies that endocytosis mediated by binding of ligands with a Gal/Gal-NAc terminal to ASGPR is regulated by calcium ion (Kim S H, Goto M, Akaike T. J Biol Chem; 276:35312-35319. (2001)).

As Gal/GalNAc has specificity to hepatic lectin, a radiopharmaceutical where a radioactive isotope is bound to a Gal/GalNAc glycoprotein can be successfully positioned to the liver cells and be endocytosed by the liver cells, thus achieving a purpose of function imaging or radiotherapy. Presently, a ah-GalNAc saccharide group has been prepared (Lee, R. T.; Wong, T. C. and Lee, Y. C., J. Carbohydrate Chem., 5, 343-357 (1986)), with a preparation process as follows. However, the preparation of the ah-GalNAc saccharide group has disadvantages below.

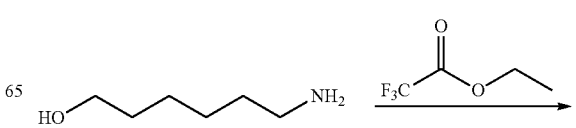

-continued

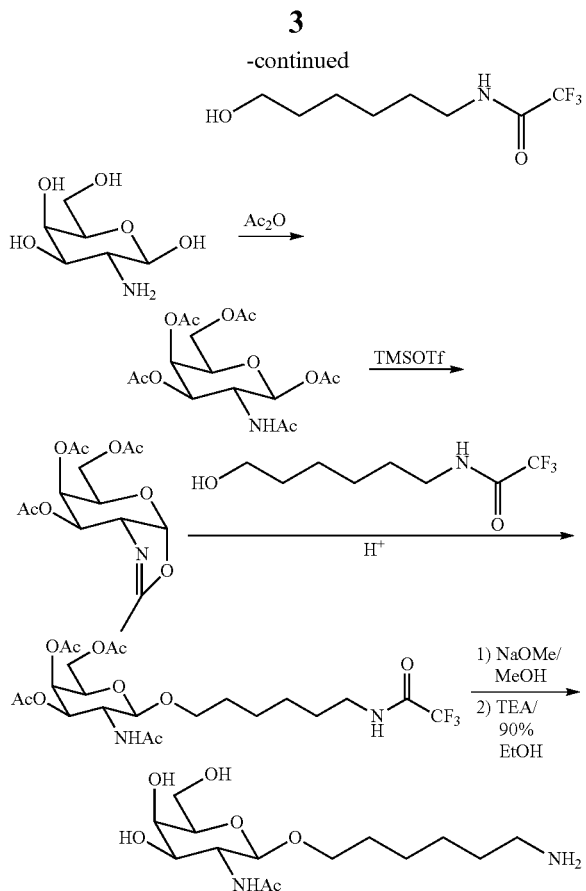

1. Synthesis methods in literatures are mainly directed to biochemistry field, and are not convenient for common organic synthesis laboratories.

2. There are many amino protecting groups, and thus selection of the amino protecting group is dependent on use of a protected compound. During synthesis of ah-GalNAc in literatures, an amino group in 6-amino hexanol is protected with trifluoacetyl, and the protecting group needs to be removed subsequently, which is inconvenient for treatment.

3. In the methods in literatures, LC columns made of expensive resins such as Sephadex LH-20 are requred for separation and purification. However, Sephadex LH-20 is very expensive and cannot be afforded by common laboratories, so the cost is high in terms of economic.

Furthermore, no attmpt is made to inject ASGPR contrast medium or other novel contrast agents with high specificity for liver into a human body currently. Combination of ASGPR contrast medium with the PET-CT technology, in cooperation with a receptor binding bifunctional compound may be one of important directions in development of liver function display using imaging methods. However, there is no contrast medium in nuclear medicine for a liver cell receptor formed by combining galactosamine (Gal) and N-acetylgalactosamine (GalNAc) with $N_2S_2$ ligand.

SUMMARY OF THE INVENTION

In view of disadvantages of conventional imaging agents in nuclear medicine, the present invention is directed to a bifunctional compound with a monosaccharide and a $N_2S_2$ ligand, and broadest technical features of the present invention lie in the bifunctional compound, and a preparation method and a use thereof.

In specification and claims of the present invention, terms used herein are defined as follows.

Term "contrast medium" refers to an agent useful in imaging technology in nuclear medicine, to realize an imaging effect for tracking radiopharmaceuticals or organ or tissue lesions with radiant rays emitted during decay of radionuclides in vivo.

Term "targeting agent" refers to a chemical or biological substance (including a nucleic acid, a protein, and a peptide) able to selectively or specifically act on tumor tissues or cells.

Term "ASGPR" refers to a receptor exiting on surface of liver cells of a mammal at a number of about 200,000, and having a specific affinity for galactosamine (Gal) and N-acetylgalactosamine (GalNAc). An affinity for the receptor of a polysubstrate is much higher than that of a mono-substrate, as found by academician Li Yuanchuan, especially when a substrate is that containing three galactosamine or N-acetylgalactosamine, the affinity of the substrate for ASGPR on surface of liver cells is much stronger, and is almost 106 times that of a single N-acetylgalactosamine substrate.

In an aspect, the present invention provides a bifunctional compound with a monosaccharide and a $N_2S_2$ ligand, which has a structure below:

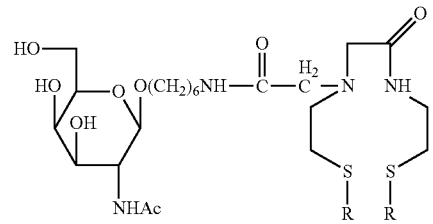

in which, R is hydrogen or a thiol protecting group.

In some embodiments, in the bifunctional compound, the thiol protecting group is selected from a group consisting of phenylcarbonyl ($COC_6H_5$) and methoxybenzyl ($CH_2C_6H_4OCH_3$).

The bifunctional compound of the present invention contains a $N_2S_2$ ligand, for linking a radionuclide such as technetium or rhenium, to form a neutral complex useful as a radiopharmaceutical.

Furthermore, the bifunctional compound contains aminohexylacetyl galactosamine (ah-GalNAc$_4$), which has very good affinity for asialoglycoprotein receptor (ASGPR) on liver cells.

In another aspect, the present invention provides a bifunctional compound with a monosaccharide and a $N_2S_2$ ligand, which has a structure below:

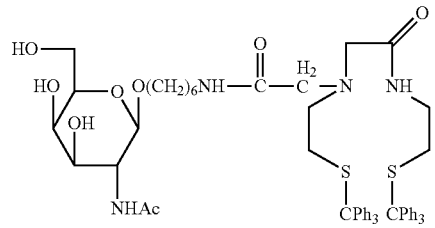

Thiol in the bifunctional compound of the present invention is protected with a thiol protecting group triphenylmethyl ($CPh_3$), and thus the bifunctional compound is stable and convenient for storage. When the bifunctional compound forms a complex with rhenium or technetium, the protecting group (CPh$_3$) of thiol leaves from the compound automatically in the complexing reaction, which is very convenient.

In another aspect, the present invention provides a method for preparing a bifunctional compound with a monosaccharide and a N$_2$S$_2$ ligand, comprising:

(1) preparing an organic ligand of Chemical Formula I;

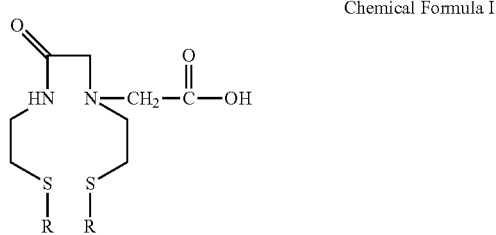

Chemical Formula I (2) preparing a galactopyranoside of Chemical Formula II; and

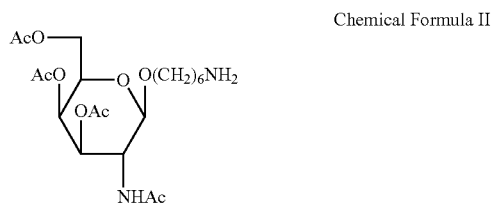

Chemical Formula II (3) activating a carboxyl group in the organic ligand of Chemical Formula I, and reacting the activated carboxyl group with the galactopyranoside of Chemical Formula II through amidation, and then hydrolyzing a resulting product.

In some embodiments, thiol in the organic ligand in (1) is protected in advance. In a specific embodiment, a thiol protecting group useful in protection of thiol is selected from a group consisting of phenylcarbonyl (COC$_6$H$_5$), methoxybenzyl (CH$_2$C$_6$H$_4$OCH$_3$), and triphenylmethyl.

In some embodiments, an amino group in (CH$_2$)$_6$NH$_2$ of the galactopyranoside in (2) is protected in advance. In a specific embodiment, an amino protecting group useful in protection of the amino group is benzyl chlorocarbonate, di-tert-butyl-dicarbonate, or ethyl trifluoroacetate.

In some embodiments, the galactopyranoside in (2) is obtained by hydrogenating of a compound of Chemical Formula III, and then separating and purifying through liquid chromatography (LC).

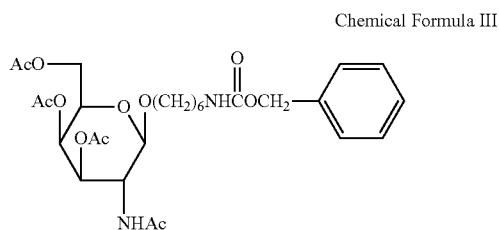

Chemical Formula III

In a specific embodiment, silica gel is used as a column in LC.

In the preparation method of the present invention, as benzyl chlorocarbonate has a property of ease in leaving from the compound, without influencing other functional groups in the molecule in hydrogenation, benzyl chlorocarbonate is selected as the amino protecting group, to protect the amino group in (CH$_2$)$_6$NH$_2$ of the galactopyranoside in (2).

In the preparation method of the present invention, in principle, the galactopyranoside obtained through hydrogenation of the compound of Chemical Formula III does not need to be separated and purified. If the compound of Chemical Formula III is pure, merely toluene is generated in hydrogenation, and toluene is highly volatile, so it will be volatilized completely without remaining during concentration. However, if the compound of Chemical Formula III is not pure enough, the galactopyranoside obtained after hydrogenation needs to be separated and purified. In the present invention, silica gel is used to fabricate an LC column, and good effect is achieved without using expensive synthetic resin (such as Sephadex LH-20 resin) for separation and purification, and thus preparation cost is significantly reduced.

In another aspect, the present invention further provides a pharmaceutical composition, which includes:

the bifunctional compound above; and an adduct, being a radionuclide or a targeting agent, or a combination thereof.

In some embodiments, the radionuclide is selected from technetium (Tc), rhenium (Re), indium (In), and a combination thereof. In some specific embodiments, a compound of technetium (Tc), rhenium (Re), indium (In) refers to an oxide, for example, TcO$^{3+}$ or ReO$^{3+}$.

In some embodiments, the targeting agent refers to a peptide or a protein.

As the pharmaceutical composition of the present invention contains the bifunctional compound able to be linked to a peptide or a protein, for example, ASGPR on surface of liver cells, as well as to TcO$^{3+}$ or ReO$^{3+}$, thus being applicable in preparing technetium or rhenium labeled radiopharmaceuticals.

In another aspect, the present invention provides a use of a bifunctional compound with a monosaccharide and a N$_2$S$_2$ ligand, in which the bifunctional compound above is linked to a radionuclide and an ASGPR on the surface of liver cells, to serve as a novel contrast medium or a radiotherapeutic agent for liver cell fibrosis in nuclear medicine.

Details of one or more embodiments of the present invention will be described in details below. Other features and advantages of the present invention will be apparent from detailed description and claims below.

The above general description and the following detailed description can be understood with reference to examples, and provide further illustration of subjects as claimed in the present invention.

BRIEF DESCRIPTION OF THE DRAWINGS

The present invention will become more fully understood from the detailed description given herein below for illustration only, and thus are not limitative of the present invention, and wherein:

FIG. 4A is a $^1$H NMR (CDCl$_3$) spectrum of Compound 4 and provides analysis data of Compound 4 according to an embodiment of the present invention;

FIG. 5B is a $^{13}$C NMR (CD$_3$OD) spectrum of Compound 5 and provides analysis data of Compound 5 according to an embodiment of the present invention;

FIG. 9A is a $^1$H NMR (CD$_3$OD) spectrum of Compound 9 and provides analysis data of Compound 9 according to an embodiment of the present invention;

DETAILED DESCRIPTION OF THE INVENTION

Figure 1A:
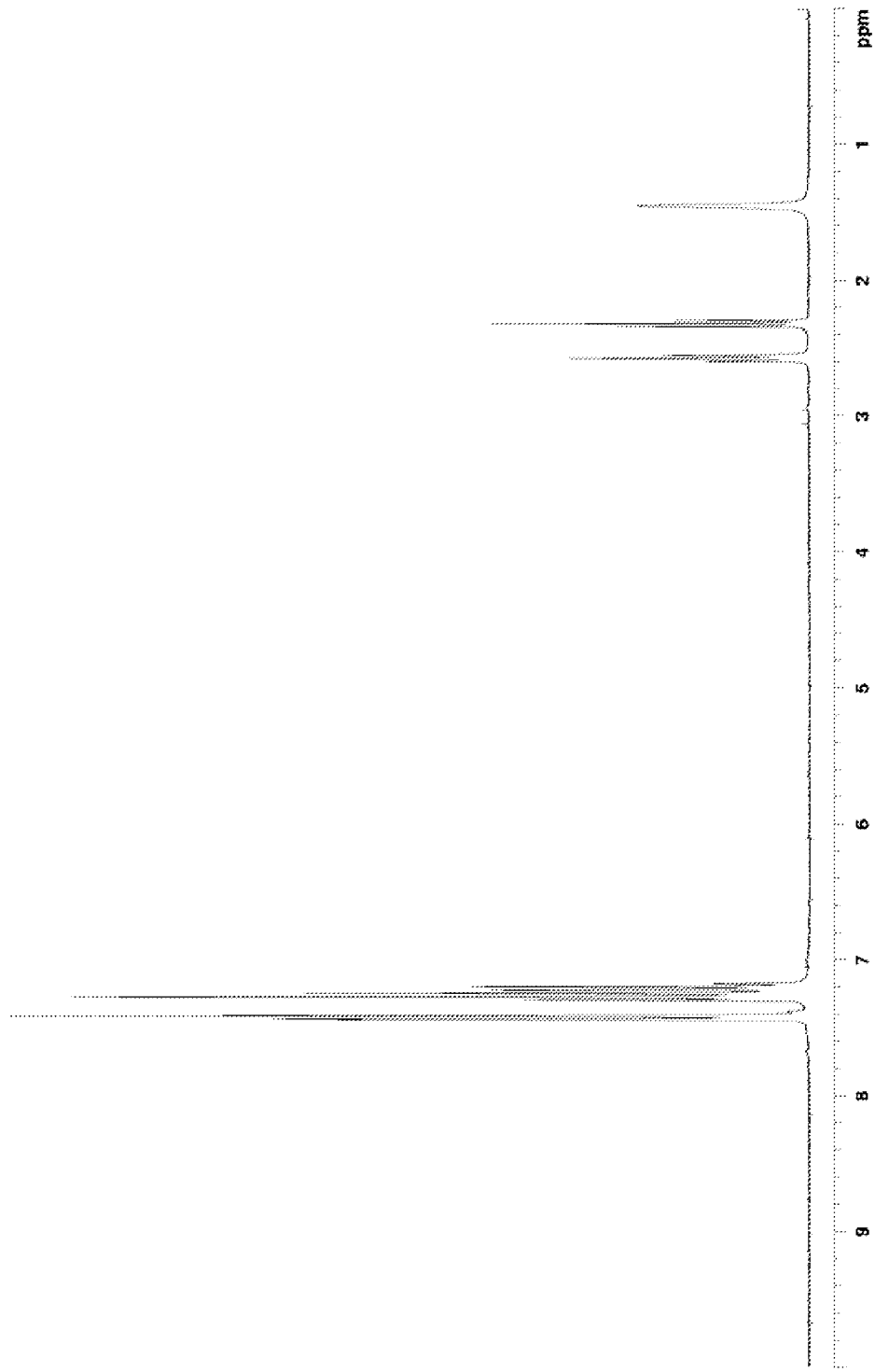
FIG. 1A is a $^1$H NMR (CDCl$_3$) spectrum of Compound 1 and provides analysis data of Compound 1 according to an embodiment of the present invention.

In order to make features and effects of the present invention clearer and more comprehensible, the present invention is illustrated with reference to preferred embodiments below and appended drawings.

In a preparation process according to an embodiment of the present invention, thiol in 2-thioethylamine hydrochloride as a starting reactant is protected first, to synthesize Compound 1, and then Compound 1 is esterified with chloroacetyl chloride, to obtain Compound 2. Compound 2 and Compound 1 are subjected to a substitution reaction, to generate an intermediate Compound 3. Then, Compound 3 and methyl bromoacetate are subjected to a substitution reaction, to obtain Compound 4. Compound 4 is hydrolyzed, to generate Compound 5. A scheme is as follows.

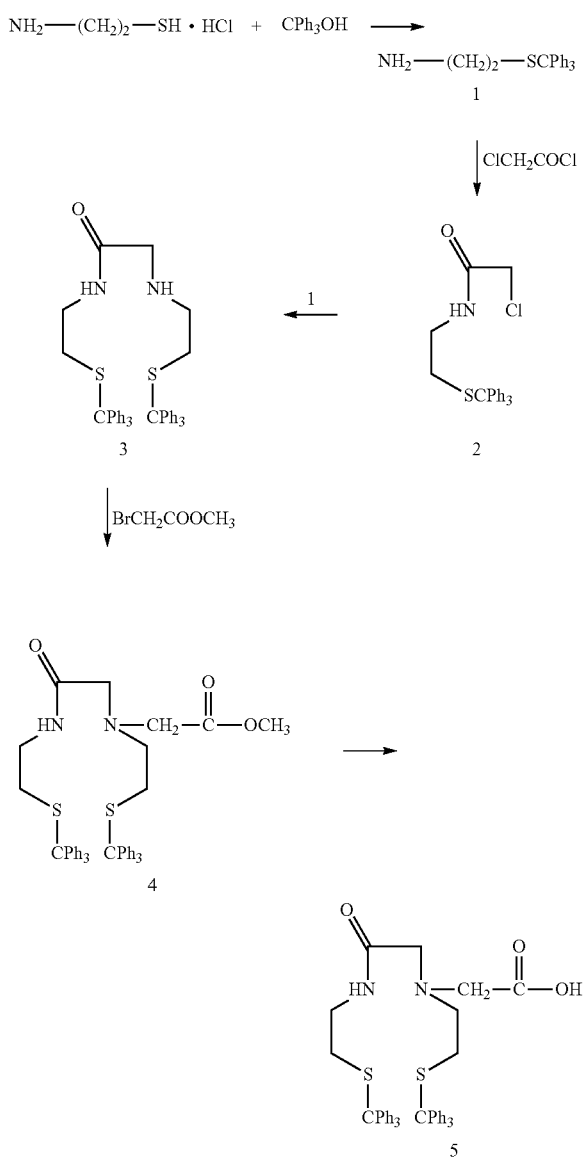

Then, an amino group in 6-aminohexyl is protected with benzyl chlorocarbonate, to generate Compound 6. N-acetyl-D-galactosamine and acetyl chloride are subjected to substitution and esterification reaction at 10° C., to generate Compound 7. Compound 6 and Compound 7 are subjected to a substitution reaction in presence of mercury cyanide as a catalyst, to generate Compound 8. With Pd/C as a catalyst, Compound 8 is hydrogenated and reduced into Compound 9. A scheme is as follows.

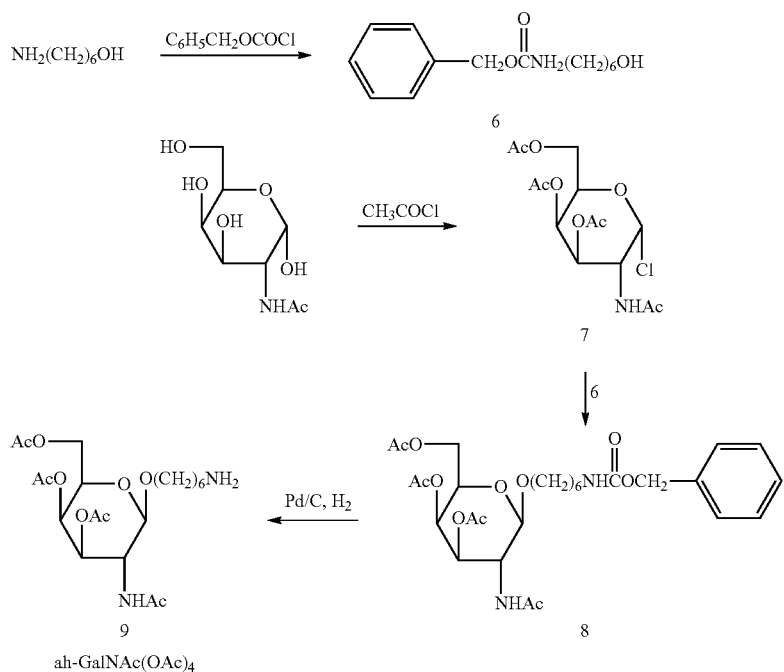

Then, Compound 5 and Compound 9 are reacted through amidation, to obtain a product Compound 10, which is then hydrolyzed, to obtain a final product. A scheme is as follows.

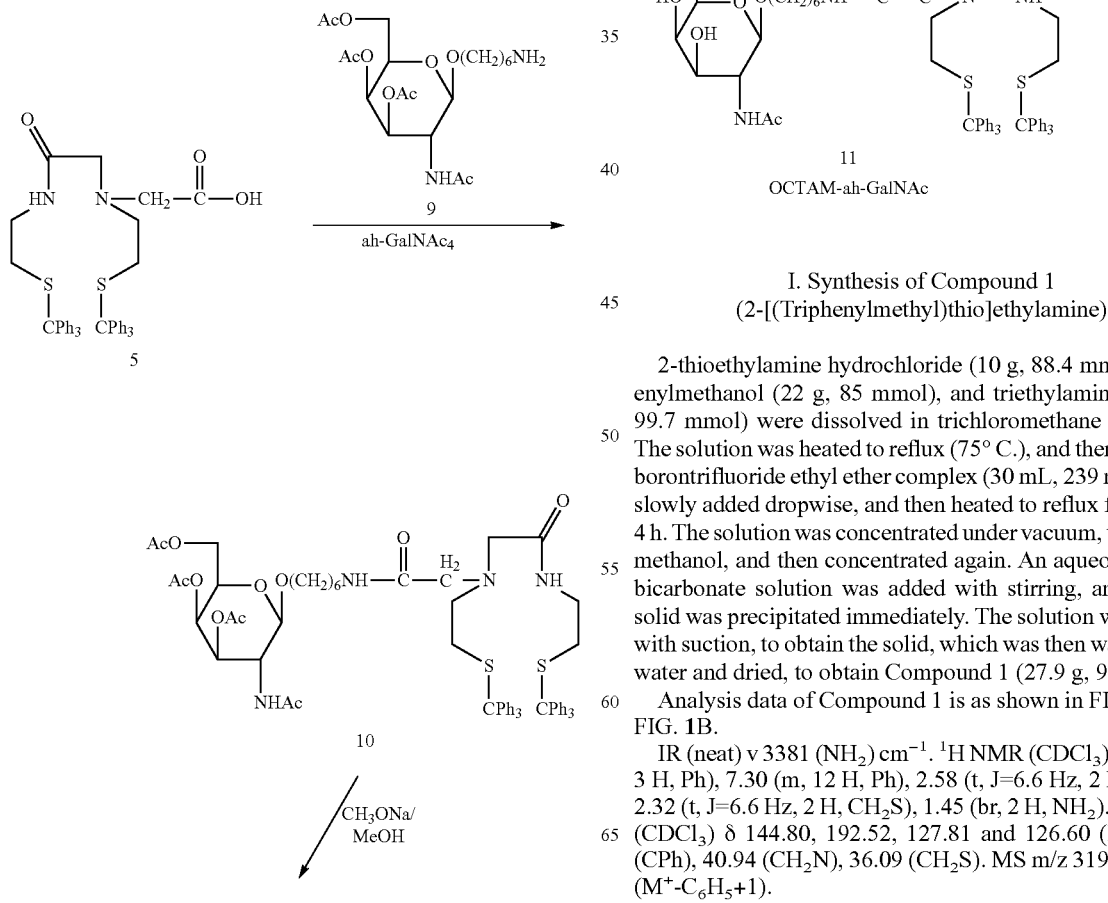

I. Synthesis of Compound 1 (2-[(Triphenylmethyl)thio]ethylamine)

2-thioethylamine hydrochloride (10 g, 88.4 mmol), triphenylmethanol (22 g, 85 mmol), and triethylamine (14 mL, 99.7 mmol) were dissolved in trichloromethane (100 mL). The solution was heated to reflux (75° C.), and then a catalyst borontrifluoride ethyl ether complex (30 mL, 239 mmol) was slowly added dropwise, and then heated to reflux for another 4 h. The solution was concentrated under vacuum, taken up in methanol, and then concentrated again. An aqueous sodium bicarbonate solution was added with stirring, and a white solid was precipitated immediately. The solution was filtered with suction, to obtain the solid, which was then washed with water and dried, to obtain Compound 1 (27.9 g, 99%).

Figure 1B:
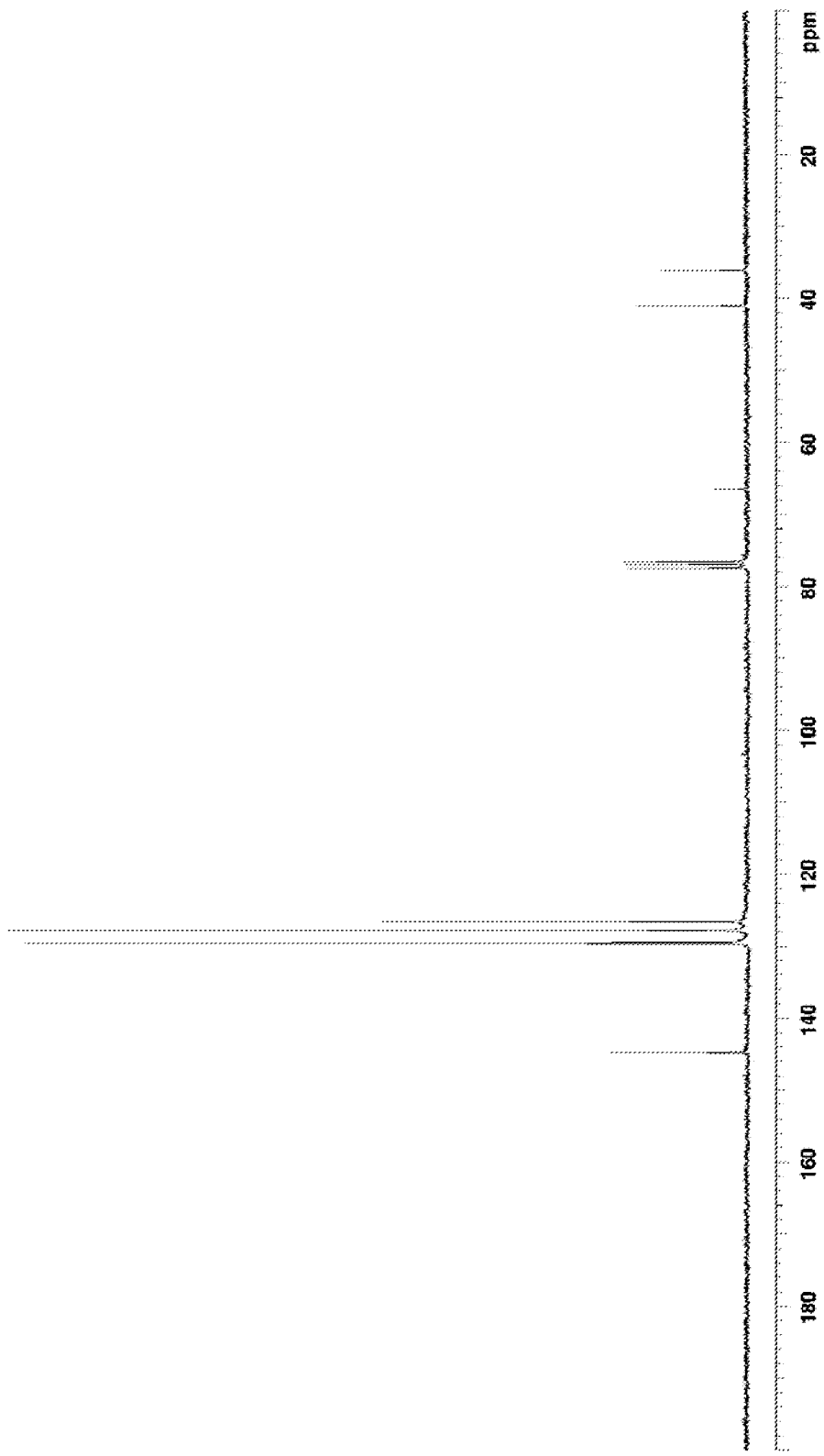
FIG. 1B is a $^{13}$C NMR (CDCl$_3$) spectrum of Compound 1 and provides analysis data of Compound 1 according to an embodiment of the present invention.

Analysis data of Compound 1 is as shown in FIG. 1A and FIG. 1B.

IR (neat) v 3381 ($NH_2$) $cm^{-1}$. $^1H$ NMR ($CDCl_3$) δ 7.42 (m, 3 H, Ph), 7.30 (m, 12 H, Ph), 2.58 (t, J=6.6 Hz, 2 H, $CH_2N$), 2.32 (t, J=6.6 Hz, 2 H, $CH_2S$), 1.45 (br, 2 H, $NH_2$). $^{13}C$ NMR ($CDCl_3$) δ 144.80, 192.52, 127.81 and 126.60 (Ph), 66.51 (CPh), 40.94 ($CH_2N$), 36.09 ($CH_2S$). MS m/z 319 ($M^+$), 243 ($M^+$-$C_6H_5$+1).

II. Synthesis of Compound 2 (N-[2-((triphenylmethyl)thio)ethyl]chloroacetamide)

Compound 1 (2.62 g, 8.2 mmol) and triethylamine (1.38 mL, 9.8 mmol) were dissolved in trichloromethane (80 mL). While cooling in an ice bath, a solution of chloroacetyl chloride (0.78 mL, 9.8 mmol) dissolved in trichloromethane (10 mL) was slowly added dropwise. After addition, the solution was stirred at room temperature for 2 h, and then an organic phase was washed with 1 N HCl solution (120 mL), a saturated aqueous sodium carbonate solution (100 mL), and water (100 mL) in sequence. The organic phase was dried over $Na_2SO_4$ and concentrated under vacuum, to obtain Compound 2 (2.81 g, 86.6%) as a yellow oil.

Figure 2A:
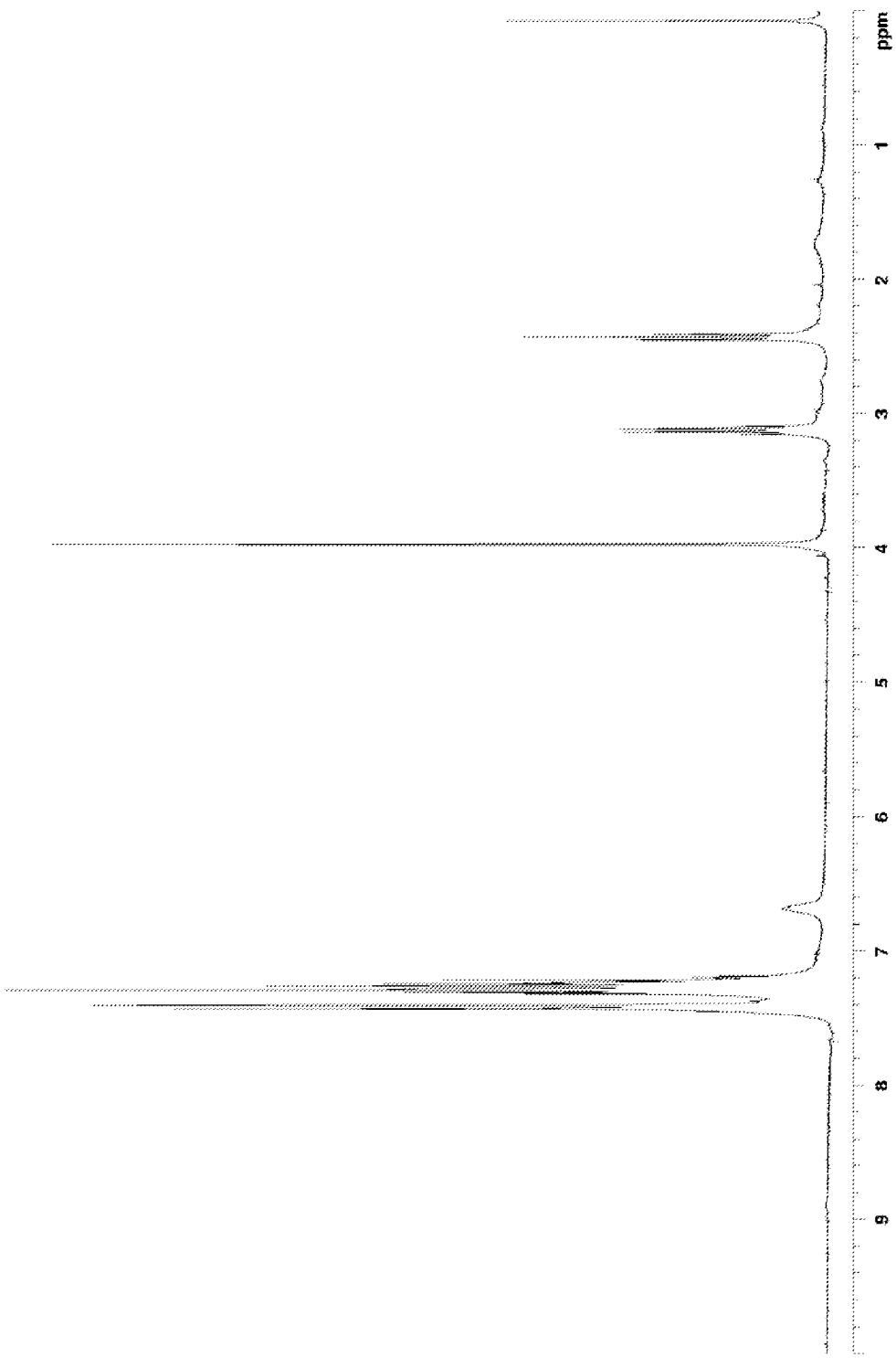
FIG. 2A is a $^1$H NMR (CDCl$_3$) spectrum of Compound 2 and provides analysis data of Compound 2 according to an embodiment of the present invention.
Figure 2B:
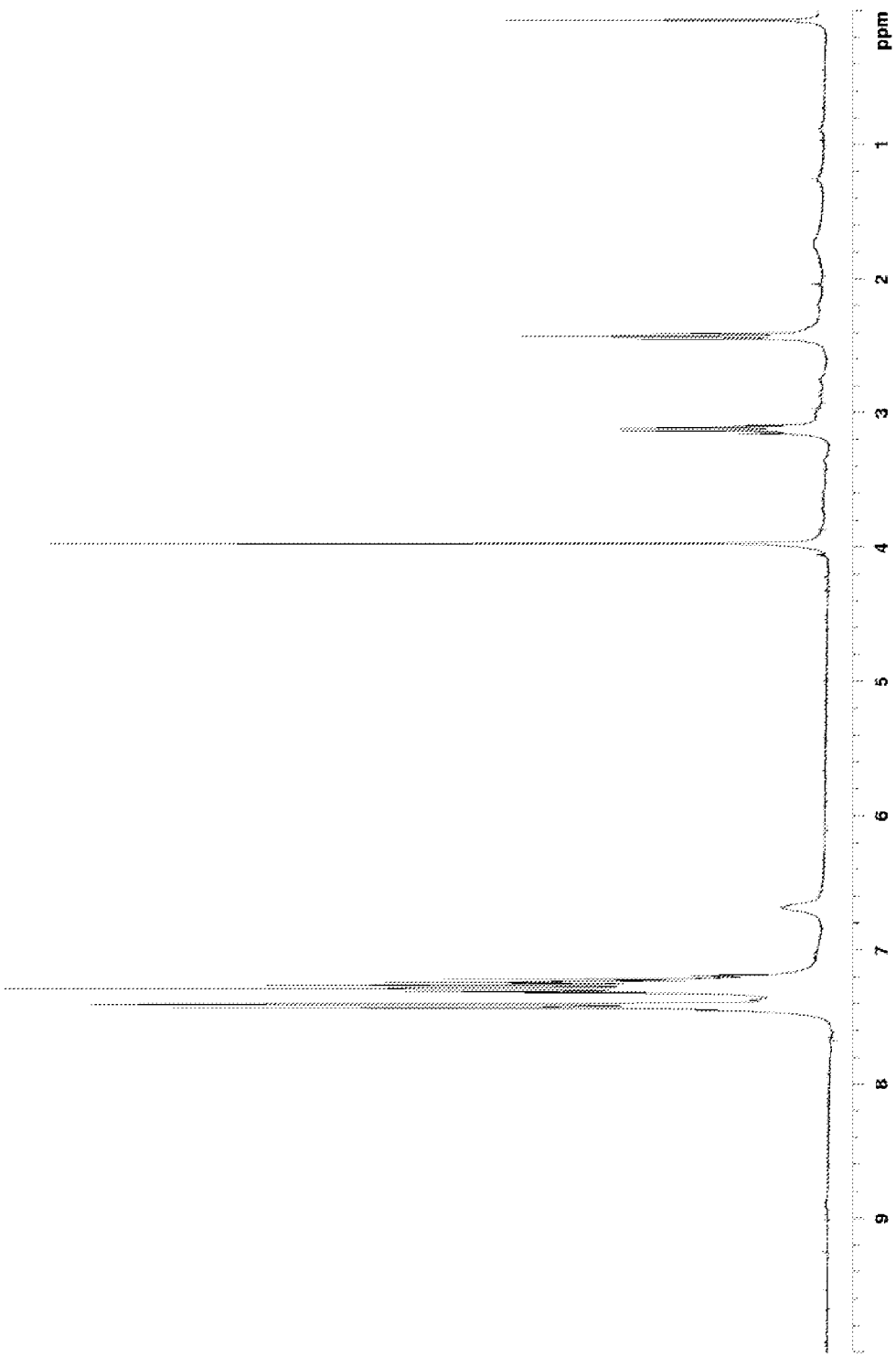
FIG. 2B is a $^{13}$C NMR (CDCl$_3$) spectrum of Compound 2 and provides analysis data of Compound 2 according to an embodiment of the present invention.

Analysis data of Compound 2 is as shown in FIG. 2A and FIG. 2B.

IR (neat) v 3413 and 3306 (NH), 1662 (CO) $cm^{-1}$. $^1H$ NMR ($CDCl_3$) δ 7.41 (m, 3 H, Ph), 7.24 (m, 12 H, Ph), 6.48 (br, 1 H, NH), 3.97 (s, 2 H, $CH_2Cl$), 3.12 (q, J=6.3 Hz, 2 H, $CH_2N$), 2.43 (t, J=6.3 Hz, 2 H, $CH_2S$). $^{13}C$ NMR ($CDCl_3$) δ165.63 (CO), 144.47, 129.48, 127.97 and 126.81 (Ph), 66.52 (CPh), 42.54 ($CH_2Cl$), 38.35 ($CH_2N$), 31.67 ($CH_2S$). MS m/z 397 and 395 ($M^+$), 243 (($CPh_3$)$^+$).

III. Synthesis of Compound 3 (N-[2-((Triphenylmethyl)thio)ethyl]-[2-((triphenylmethyl)thio)ethylamino]acetamide)

Compound 2 (2.7 g, 6.9 mmol) and Compound 1 (2.2 g, 6.9 mmol) were dissolved in dichloromethane (60 mL), and then triethylamine (1.5 mL, 10.4 mmol) was added, and heated to reflux for two days. After cooling, the solution was washed with an aqueous $NaHCO_3$ solution (60 mL), and then water (60 mL, once), and an organic layer was taken. The organic phase was dried over $Na_2SO_4$ and concentrated, and then separated and purified through LC ($SiO_2$, ethyl acetate:hexane=1:1), to obtain Compound 3 (1.1 g, 41.8%) as a pale yellow oil.

Figure 3A:
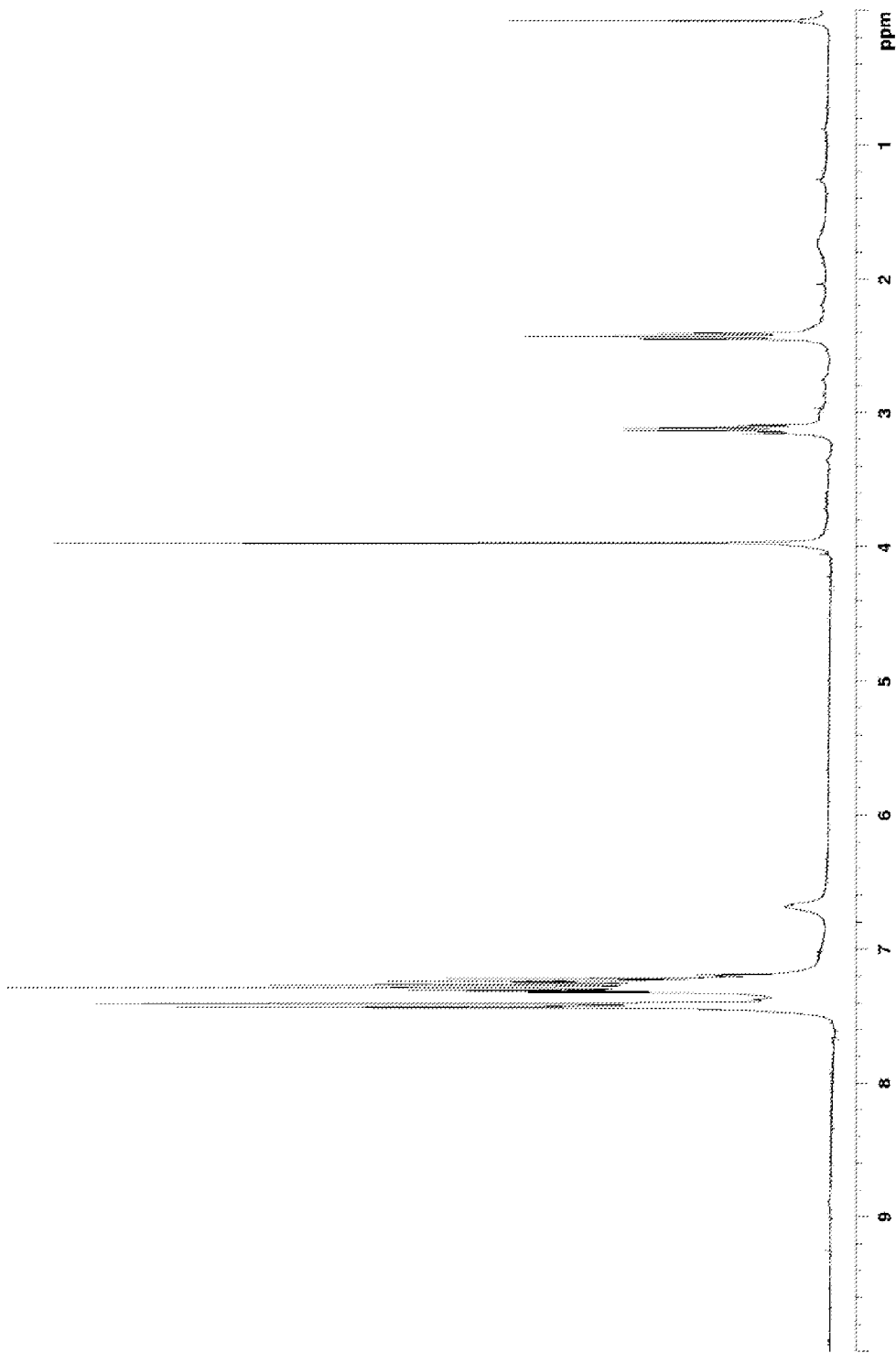
FIG. 3A is a $^1$H NMR (CDCl$_3$) spectrum of Compound 3 and provides analysis data of Compound 3 according to an embodiment of the present invention.
Figure 3B:
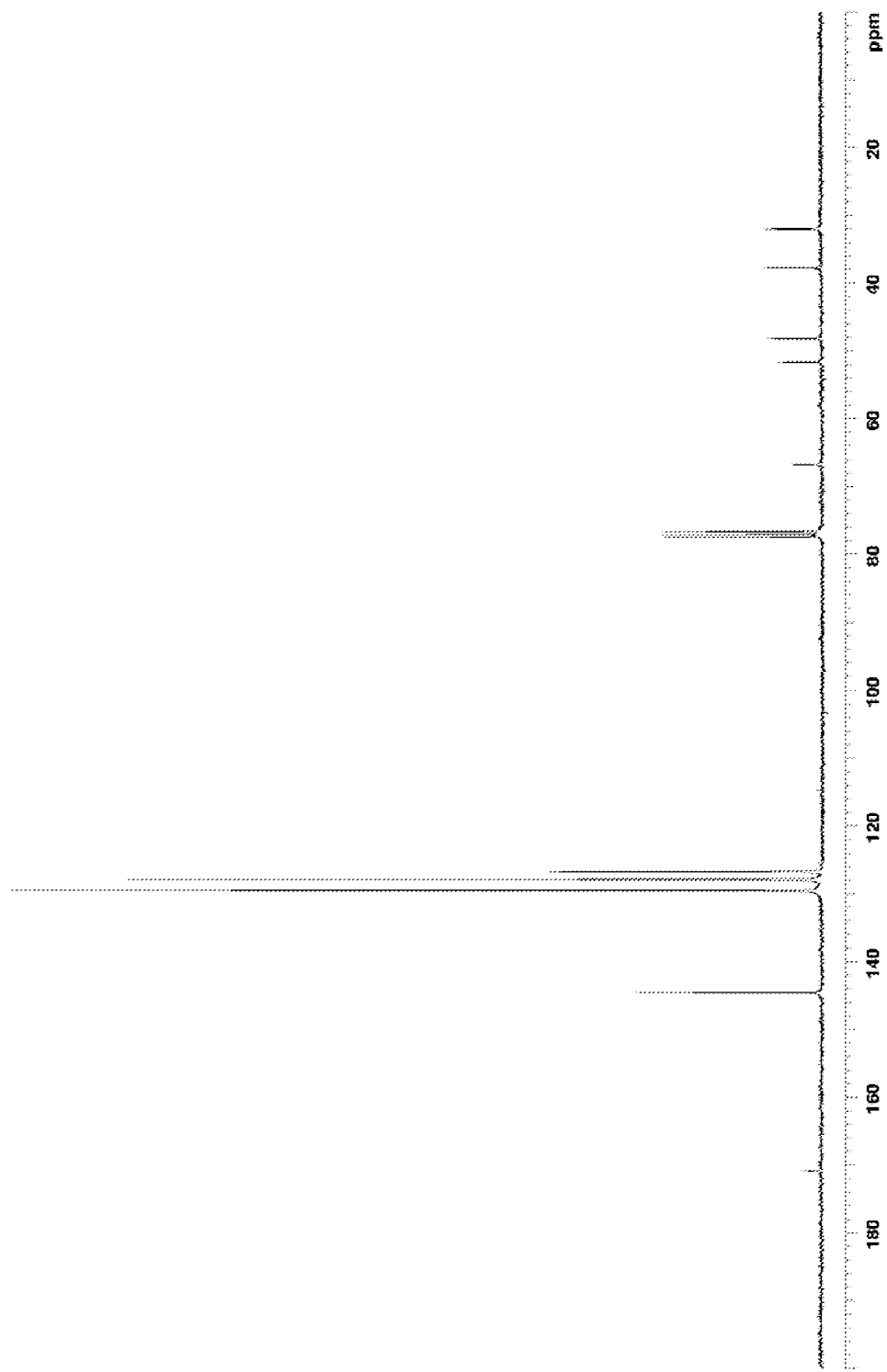
FIG. 3B is a $^{13}$C NMR (CDCl$_3$) spectrum of Compound 3 and provides analysis data of Compound 3 according to an embodiment of the present invention.

Analysis data of Compound 3 is as shown in FIG. 3A and FIG. 3B.

IR (neat) v 3330 (NH), 1670 (CO) $cm^{-1}$. $^1H$ NMR ($CDCl_3$) δ 7.42 (m, 4 H, HNCO and Ph), 7.20 (m, 12 H, Ph), 3.07 (m, 4 H, $CH_2NCO$ and $CH_2CO$), 2.38 (m, 6 H, $CH_2NHCH_2CO$ and $CH_2S$), 1.94 (br, 1 H, $NHCH_2CO$). $^{13}C$ NMR ($CDCl_3$) δ170.84 (CO), 144.61, 129.47, 127.88 and 126.69 (Ph), 66.72 and 66.65 ($CPh_3$), 51.62 ($CH_2CO$), 48.19 ($CH_2NHCH_2CO$), 37.70 ($CH_2NHCO$), 32.12 and 31.97 ($CH_2S$). MS m/z 243 (($CPH_3$)$^+$).

IV. Synthesis of Compound 4 (Methyl 3,6-diaza-5-oxo-3-[2-((triphenylmethyl)thio)ethyl]-8-[(triphenylmethyl)thio]octanoate)

Methyl bromoacetate (2.9 mL, 30.9 mmol) was added into Compound 3 (8.4 g, 12.4 mmol), triethylamine (2.6 mL, 18.6 mmol), and acetonitrile (1000 mL), and then heated to reflux (85° C.) overnight. The solution was cooled and concentrated under vacuum, a residue was dissolved in dichloromethane (100 mL), and washed with water (100 mL), and then an aqueous phase was discarded. An organic phase was dried over $Na_2SO_4$, concentrated, and then separated and purified through LC ($SiO_2$, ethyl acetate:hexane=1:1), to obtain Compound 4 (5.0 g, 53.7%) as a pale yellow oil.

Figure 4B:
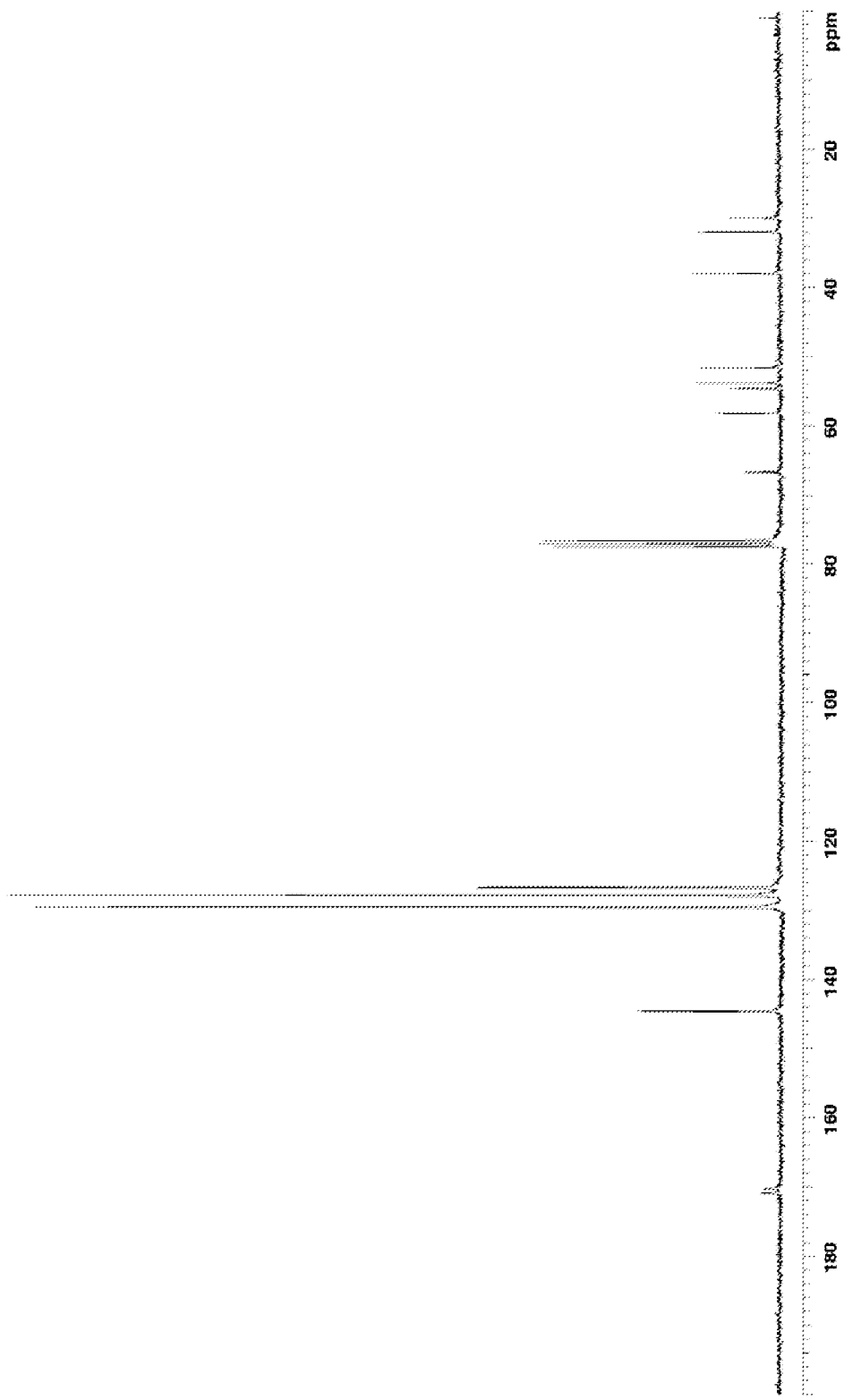
FIG. 4B is a $^{13}$C NMR (CDCl$_3$) spectrum of Compound 4 and provides analysis data of Compound 4 according to an embodiment of the present invention.

Analysis data of Compound 4 is as shown in FIG. 4A and FIG. 4B.

IR (neat) v 3349 (NH), 1743 and 1675 (CO) $cm^{-1}$. $^1H$ NMR ($CDCl_3$) δ 7.55 (NH), 7.40 (m, 3 H, Ph), 7.22 (m, 12 H, Ph), 3.61 (s, 3 H, $CH_3$), 3.20 (s, 2 H, $CH_2CO$), 3.06 (m, 4 H, $CH_2CO$ and $CH_2NH$), 2.56 (t, J=6.6 Hz, 2 H, $CH_2N$), 2.39 (t, J=6.6 Hz, $CH_2S$), 2.28 (t, J=6.6 Hz, $CH_2S$). $^{13}C$ NMR ($CDCl_3$) δ 170.89 and 170.21 (CO), 144.68, 144.57, 129.51, 129.47, 127.89, 127.86, 126.70 and 126.62 (Ph), 66.82 and 66.63 ($CPh_3$), 58.14, 54.62 and 53.72 ($CH_2$), 51.64 ($CH_3O$), 38.0 ($CH_2NH$), 31.90 and 29.99 ($CH_2S$). MS m/z 507 ($M^+$-$CPh_3$), 448 ($M^+$-$CPh_3$-$COOCH_3$).

V. Synthesis of Compound 5 (3,6-Diaza-5-oxo-3-[2-((triphenylmethyl)thio)ethyl]-8-[(triphnylmethyl)thio]octanoic acid)

Potassium hydroxide (0.5 g) was dissolved in anhydrous methanol (5 mL). Compound 4 (0.1 g, 0.133 mmol) was added and dissolved with stirring at room temperature (for about 5 h). After the solution was concentrated under vacuum at room temperature, water (2 mL) and methanol (2 mL) were added for complete dissolution, and the reaction solution was adjusted to pH 7.0 with concentrated hydrochloric acid, extracted with dichloromethane (2×10 mL), and an aqueous phase was discarded. An organic phase was dried over $Na_2SO_4$ and concentrated under vacuum, to obtain Compound 5 (98 mg, 100%) as a pale yellow oil.

Figure 5A:
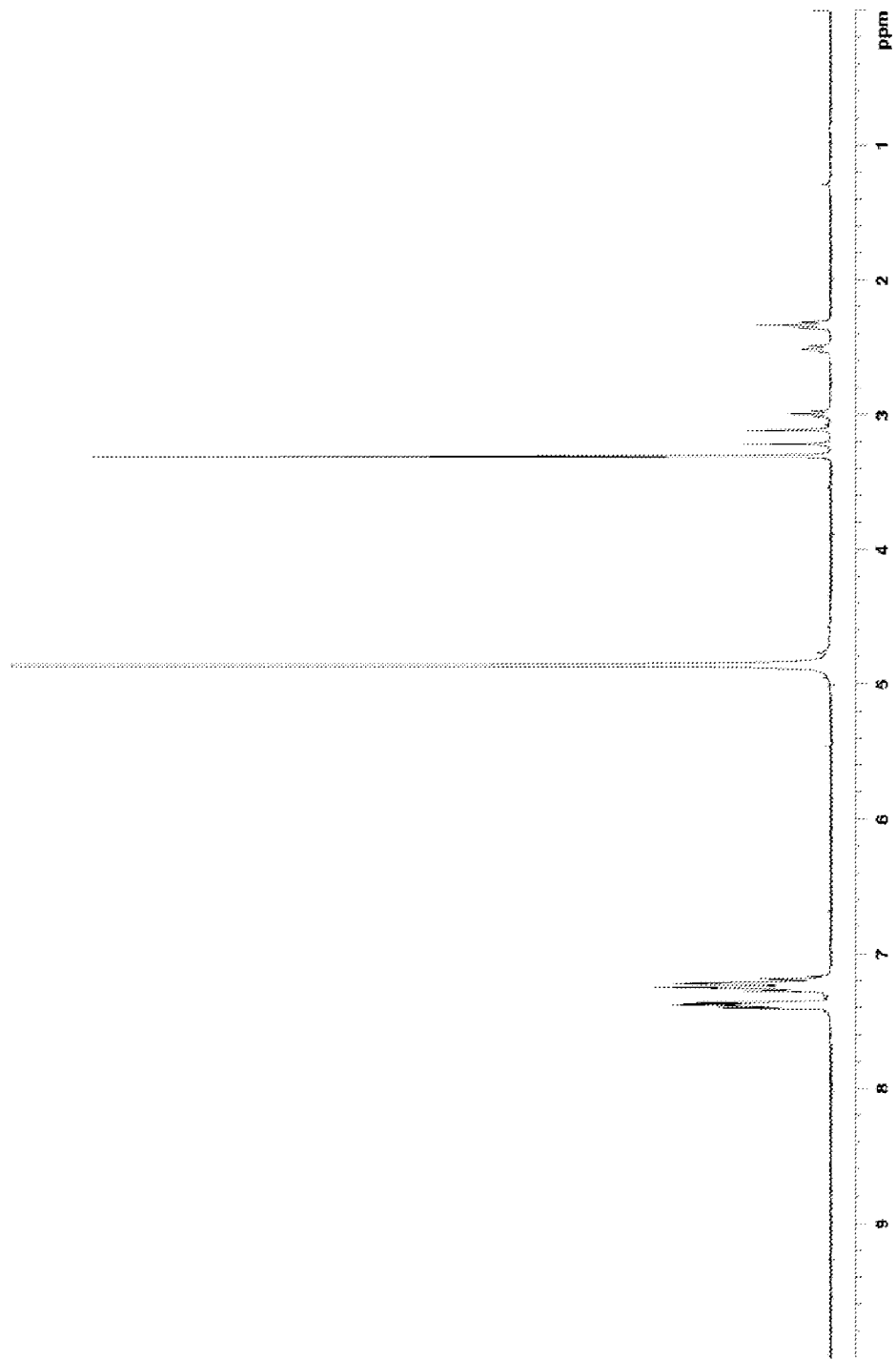
FIG. 5A is a $^1$H NMR (CD$_3$OD) spectrum of Compound 5 and provides analysis data of Compound 5 according to an embodiment of the present invention.

Analysis data of Compound 5 is as shown in FIG. 5A and FIG. 5B.

IR (neat) v 3327 (NH), 1726 and 1634 (CO) $cm^{-1}$. $^1H$ NMR ($CD_3OD$) δ 7.40 (m, 3 H, Ph), 7.25 (m, 12 H, Ph), 3.21 (s, 2 H, $CH_2$), 3.11 (s, 2 H, $CH_2$), 2.30 (t, J=6.6 Hz, 2 H, $CH_2NH$), 2.52 (t, J=6.6 Hz, 2 H, $CH_2N$), 2.34 (t, J=6.6 Hz, 4, H, $CH_2S$). $^{13}C$ NMR ($CD_3OD$) δ 173.89 and 172.97 (CO), 146.11, 130.72, 128.96, 127.87 and 127.81 (Ph), 68.09 and 67.84 ($CPh_3$), 59.0, 55.86 and 55.13 ($CH_2$), 39.12 ($CH_2NH$), 32.70 and 31.01 ($CH_2S$). MS m/z 243 (($CPh_3$)$^+$.

VI. Synthesis of Compound 6 (6-(N-Benzyloxycarbonyl)aminohexanol)

6-aminohexanol (5.9 g, 50.0 mmol) was dissolved in water (20 mL), sodium carbonate (3.2 g, 30.0 mmol) was added, and the solution was placed in an ice bath. A solution of benzyl chlorocarbonate (7.3 g, 50.0 mmol) dissolved in diethyl ether (20 mL) was slowly added dropwise. After addition, the solution was stirred at room temperature for another 2 h, and filtered, and a resulting solid was washed with a small amount of diethyl ether, and removed of solvent in a vacuum system, to obtain Product 1 (9.2 g, 73.2%).

Figure 6A:
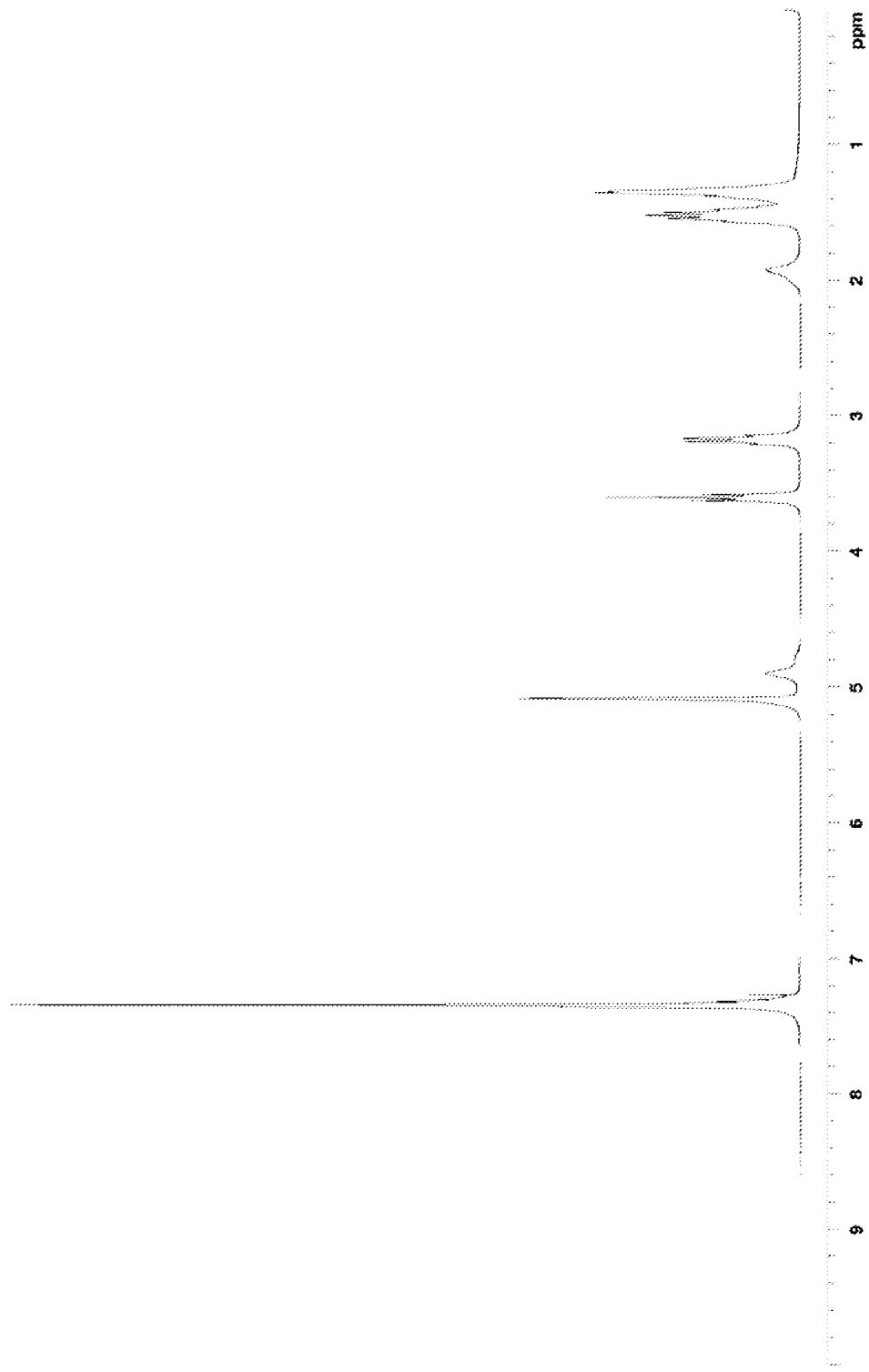
FIG. 6A is a $^1$H NMR (CDCl$_3$) spectrum of Compound 6 and provides analysis data of Compound 6 according to an embodiment of the present invention.
Figure 6B:
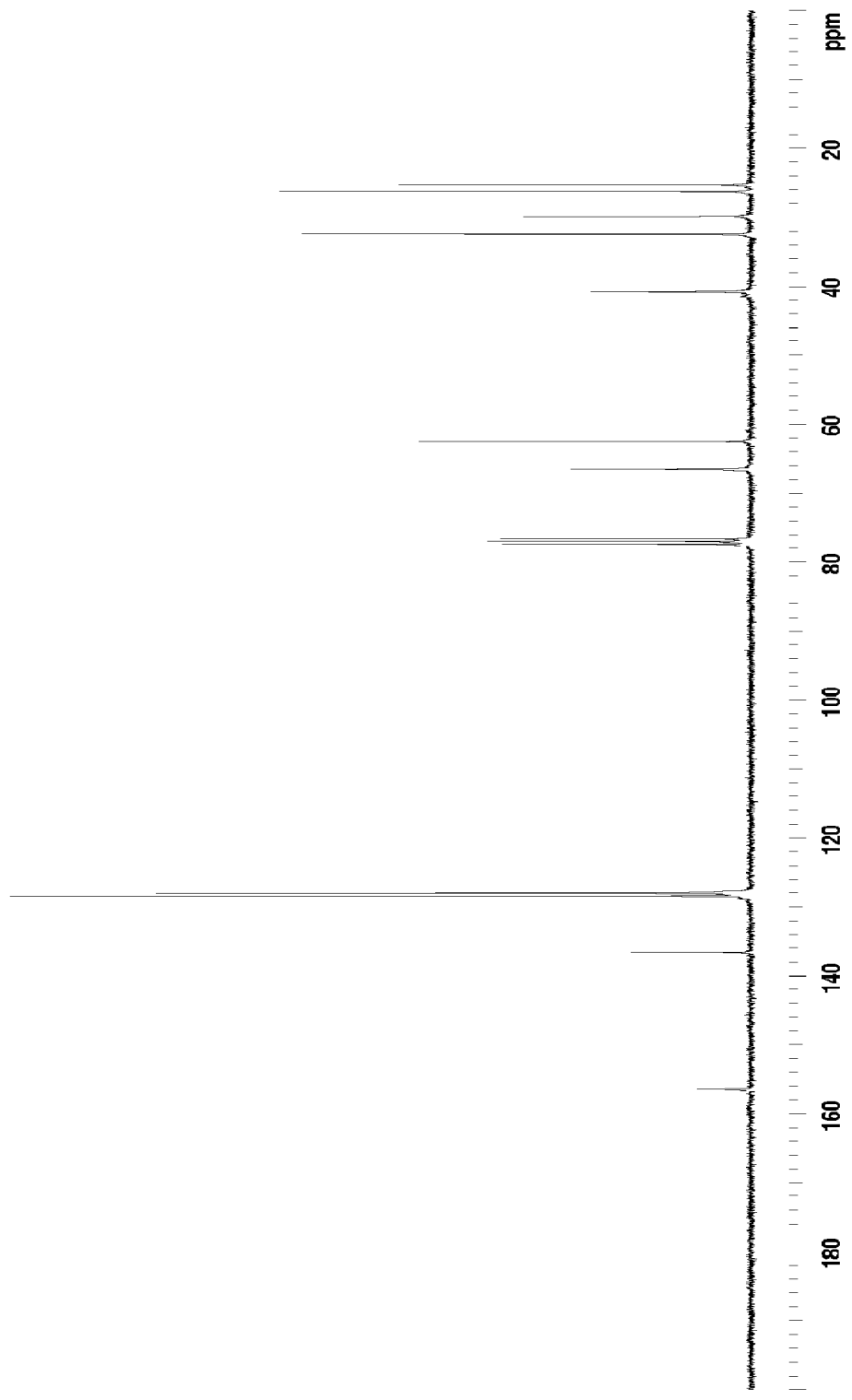
FIG. 6B is a $^{13}$C NMR (CDCl$_3$) spectrum of Compound 6 provides analysis data of Compound 6 according to an embodiment of the present invention.

Analysis data of Compound 6 is as shown in FIG. 6A and FIG. 6B.

IR (neat) v 3382 and 1530 (NH), 3336 (OH), 1688 (CO) $cm^{-1}$. $^1H$ NMR ($CDCl_3$) δ 7.34 (m, 5 H, Ph), 5.08 (s, 2 H, $PhCH_2$), 4.90 (br, 1 H, NH), 3.60 (t, J=6.5 Hz, 2 H, $CH_2OH$), 3.17 (q, J=6.6 Hz, 2 H, $NHCH_2$), 1.93 (br, 1 H, OH), 1.52 (m, 4 H, $CH_2CH_2CH_2CH_2CH_2O$), 1.35 (m, 4 H, $CH_2CH_2CH_2CH_2O$). $^{13}C$ NMR ($CDCl_3$) δ 156.45 (CO), 136.55, 128.42 and 127.99 (Ph), 66.51 ($CH_2OH$), 62.52 ($PhCH_2$), 40.82 ($NHCH_2$), 32.45 ($CH_2CH_2OH$), 29.84 ($NHCH_2CH_2$), 26.28 ($CH_2CH_2OH$), 25.22 ($CH_2CH_2CH_2OH$). MS m/z 251 ($M^+$).

VII. Synthesis of Compound 7 (2-Acetamido-3,4,6,-tri-O-acetyl-1-chloro-1,2-dideoxy-α-D-galactopyranose)

N-acetyl-D-galactosamine (3.0 g, 13.6 mmol) was added to acetyl chloride (30 mL) cooled to 0° C., sealed with a cover, placed in a thermostatic bath at 10° C. and stirred for 5 days.

Then, dichloromethane (80 mL) was added and fully mixed, and then ice water (160 mL) was added and fully stirred, till two phases are separated. An organic phase was washed with a saturated aqueous sodium bicarbonate solution (1×50 mL), and then dried over anhydrous sodium sulfate, and the solvent was evaporated under vacuum, to obtain Compound 7 (2.45 g, 51%) as a sticky oil.

Figure 7A:
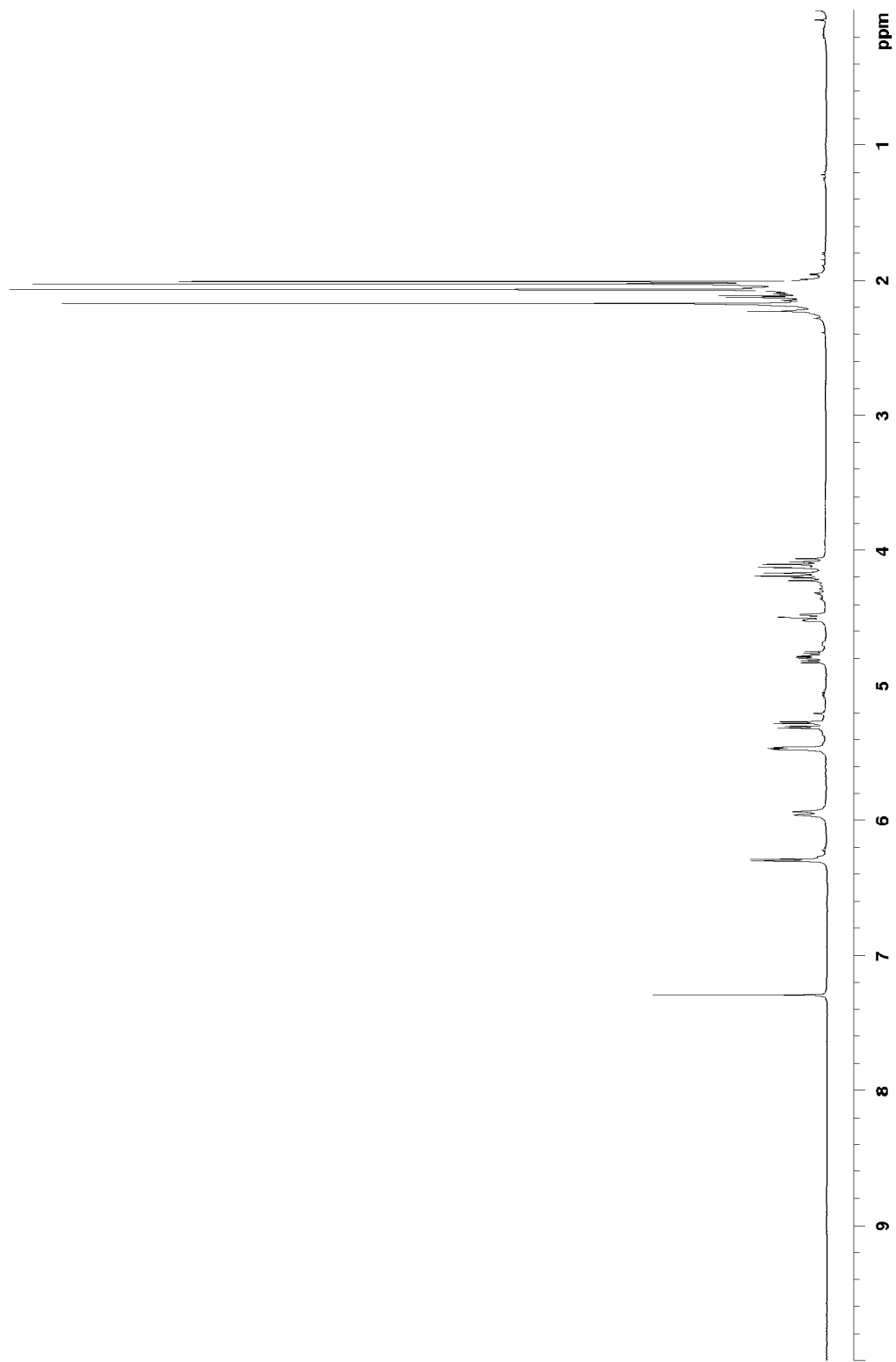
FIG. 7A is a $^1$H NMR (CDCl$_3$) spectrum of Compound 7 and provides analysis data of Compound 7 according to an embodiment of the present invention.
Figure 7B:
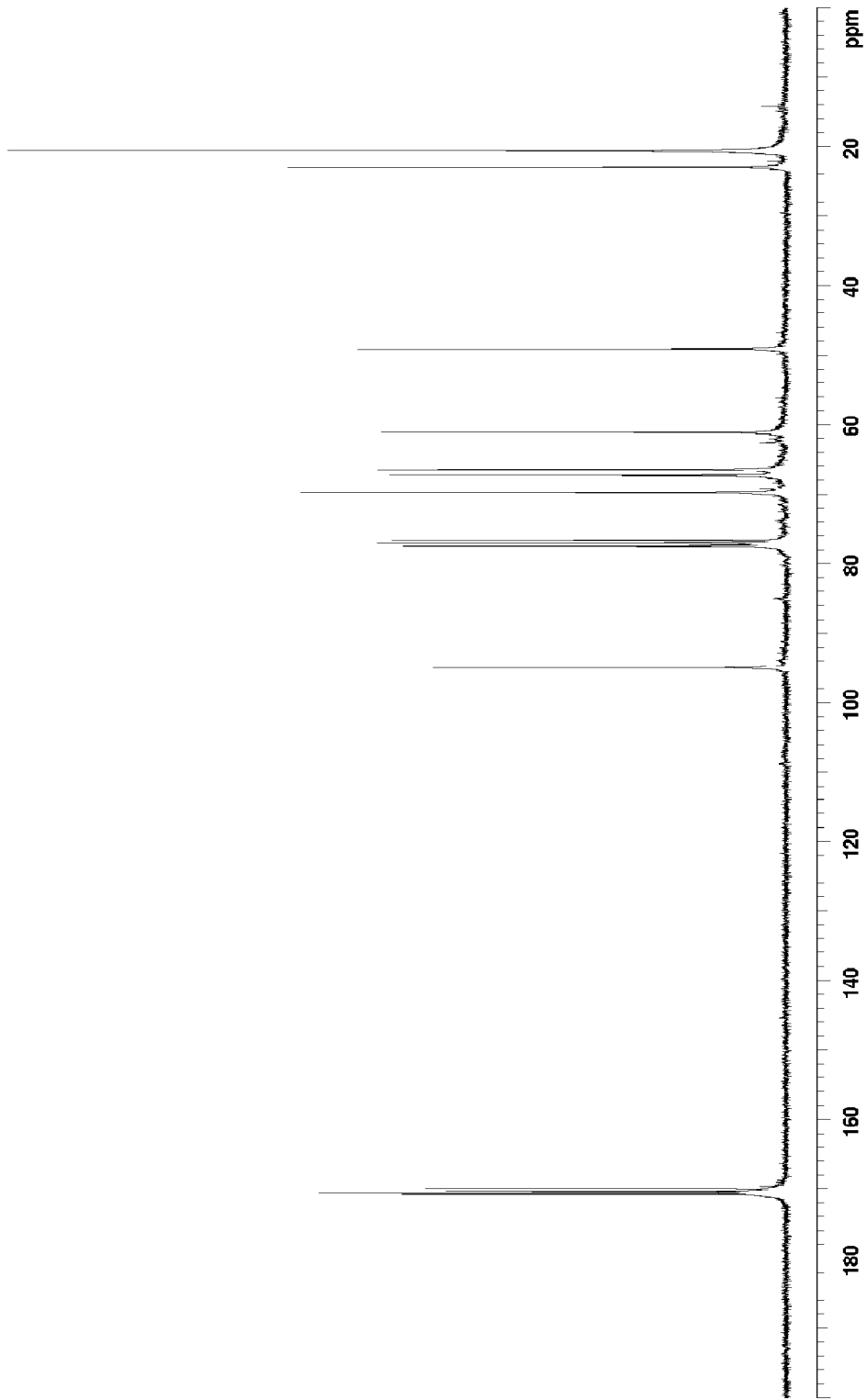
FIG. 7B is a $^{13}$C NMR (CDCl$_3$) spectrum of Compound 7.

Analysis data of Compound 7 is as shown in FIG. 7A and FIG. 7B.

IR (neat) v 3289 and 1544 (NH), 1750 and 1666 (CO) cm$^{-1}$. $^1$H NMR (CDCl$_3$) δ 6.28 (d, J=3.6 HZ, 1 H, H$_1$), 5.94 (d, J=8.7 Hz, 1 H, NH), 5.46 (dd, J=3.2 and 1.4 Hz, 1 H, H$_4$), 5.29 (dd, J=11.4 and 3.3 Hz, 1 H, H$_3$), 4.79 (m, 1 H, H$_2$), 4.48 (t, J=6.9 Hz, 1 H, H$_5$), 4.19 (m, 2 H, H$_6$), 2.17 (s, 3 H, CH$_3$), 2.10 (s, 3 H, CH$_3$), 2.03 (s, 3 H, CH$_3$), 2.01 (s, 3 H, CH$_3$). $^{13}$C NMR (CDCl$_3$) δ 170.65, 170.48, 170.26 and 169.95 (CO), 94.97 (C$_1$), 69.73 (C$_5$), 67.27 (C$_4$), 66.48 (C$_3$), 61.06 (C$_2$), 49.12 (C$_6$), 22.91, 20.56, 20.52 and 20.49 (CH$_3$). MS m/z 330 (M$^+$-Cl).

VIII. Synthesis of Compound 8 (6'-(N-Benzyloxycarbonyl)aminohexyl 2-acetamido-3,4,6-tri-O-acetyl-2-deoxy-β-D-galactopyranoside)

Compound 6 (0.72 g, 2.86 mmol), Compound 7 (1.05 g, 2.86 mmol), anhydrous calcium sulfate (0.3 g), and mercury cyanide (0.88 g, 3.5 mmol) were placed in a mixture of toluene (15 mL) and nitromethane (15 mL), stirred at room temperature for 24 h, and then filtered. A filtrate was concentrated under vacuum, and a residue was dissolved in dichloromethane (80 mL), and washed with water (2×50 mL). An organic phase was dried over anhydrous sodium sulfate, concentrated under vacuum, and separated and purified through LC (SiO$_2$, CHCl$_3$:CH$_3$OH=95:5), to obtain Compound 8 (0.58 g, 35%) as a colorless solid.

Figure 8A:
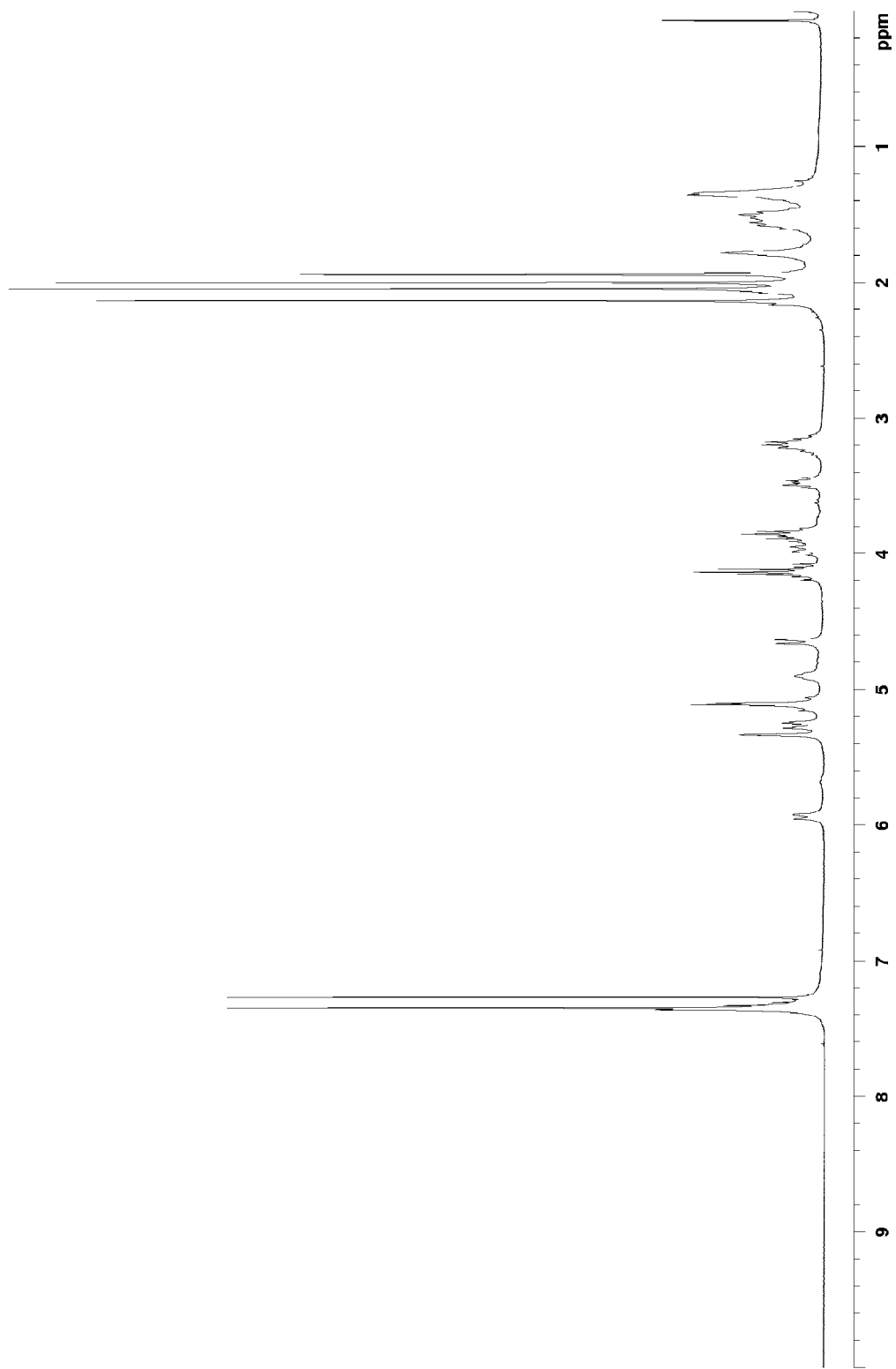
FIG. 8A is a $^1$H NMR (CDCl$_3$) spectrum of Compound 8 and provides analysis data of Compound 8 according to an embodiment of the present invention.
Figure 8B:
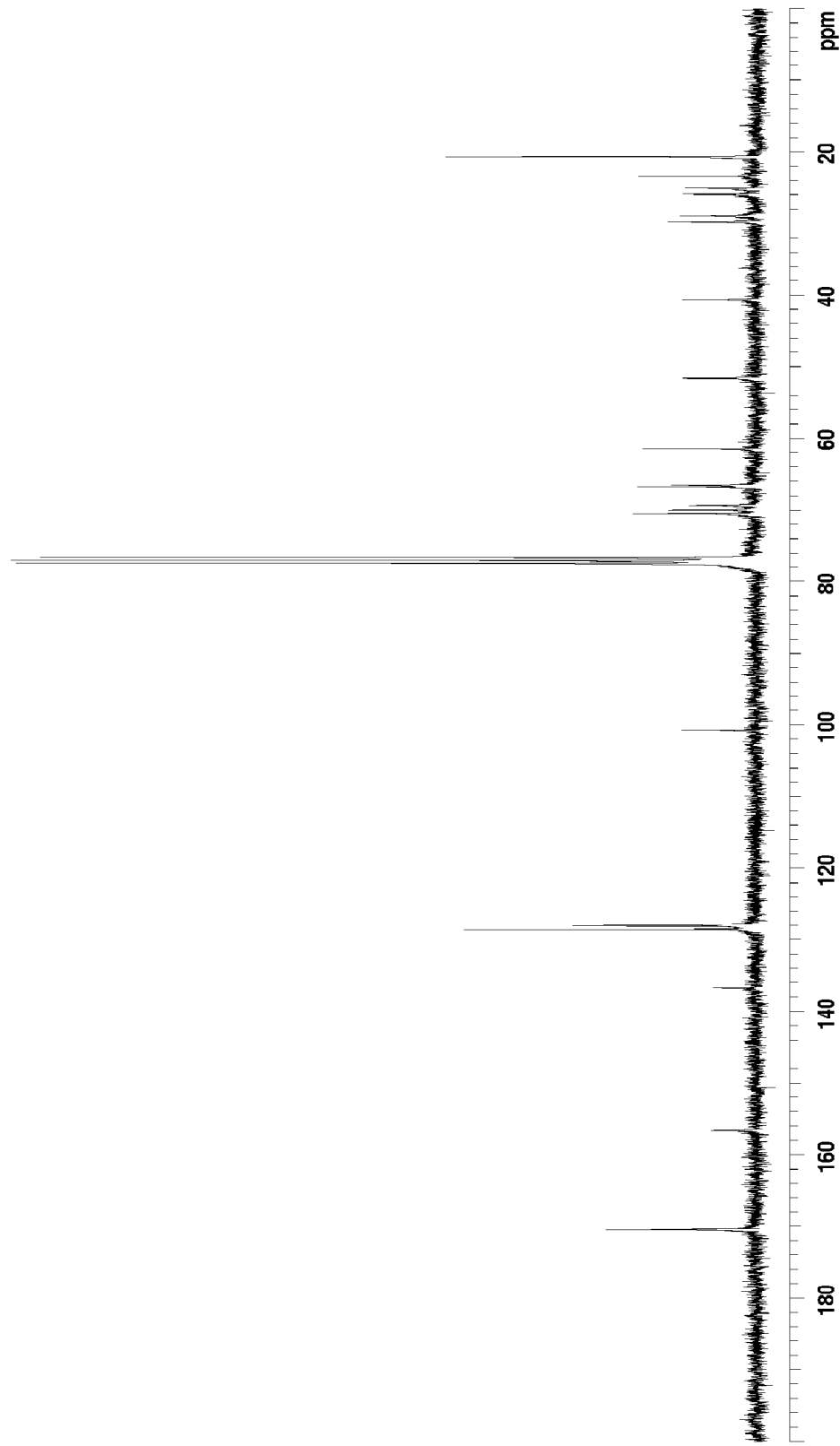
FIG. 8B is a $^{13}$C NMR (CDCl$_3$) spectrum of Compound 8 and provides analysis data of Compound 8 according to an embodiment of the present invention.
Figure 8C:
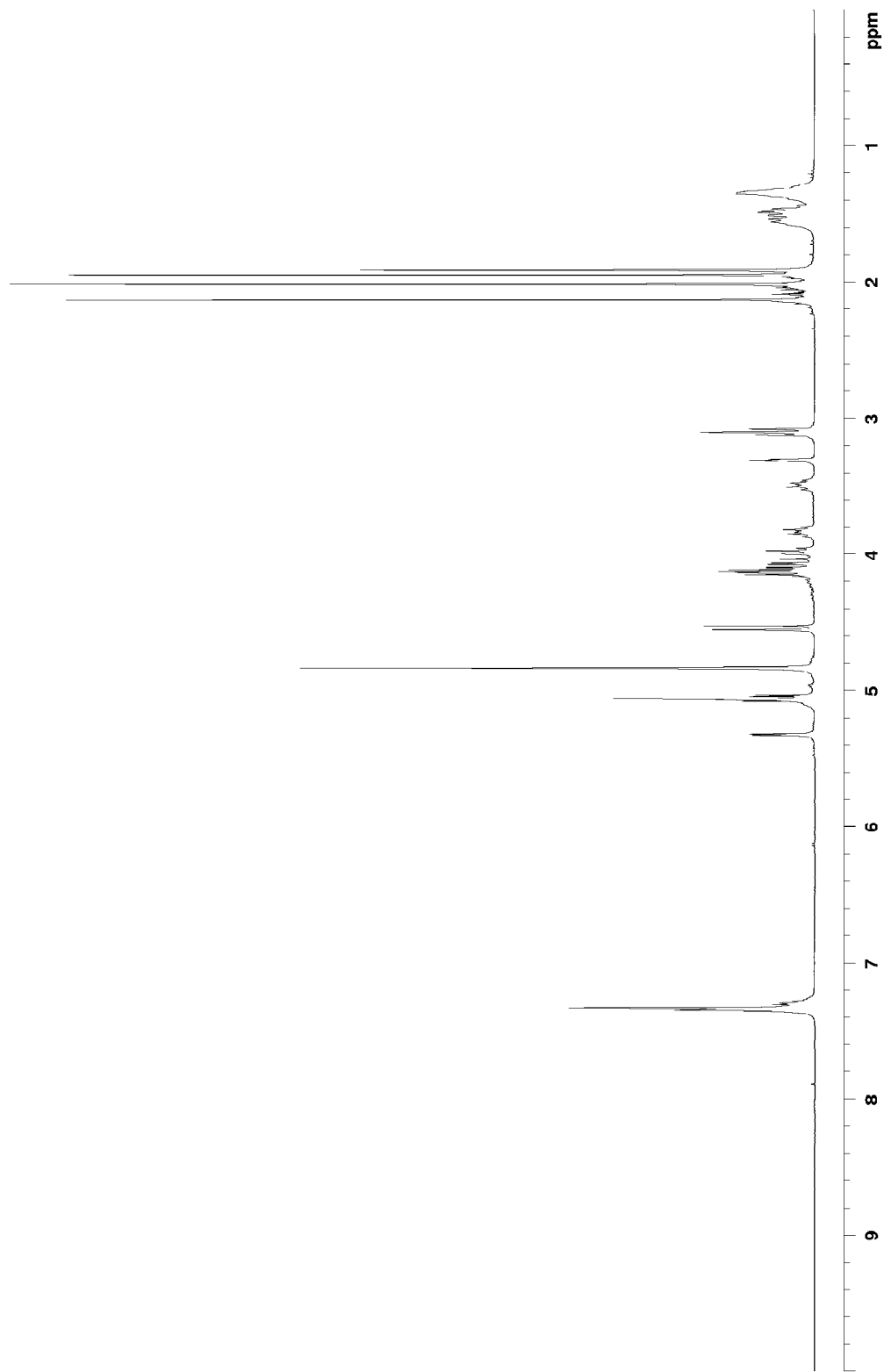
FIG. 8C is a $^1$H NMR (CD$_3$OD) spectrum of Compound 8 and provides analysis data of Compound 8 according to an embodiment of the present invention.
Figure 8D:
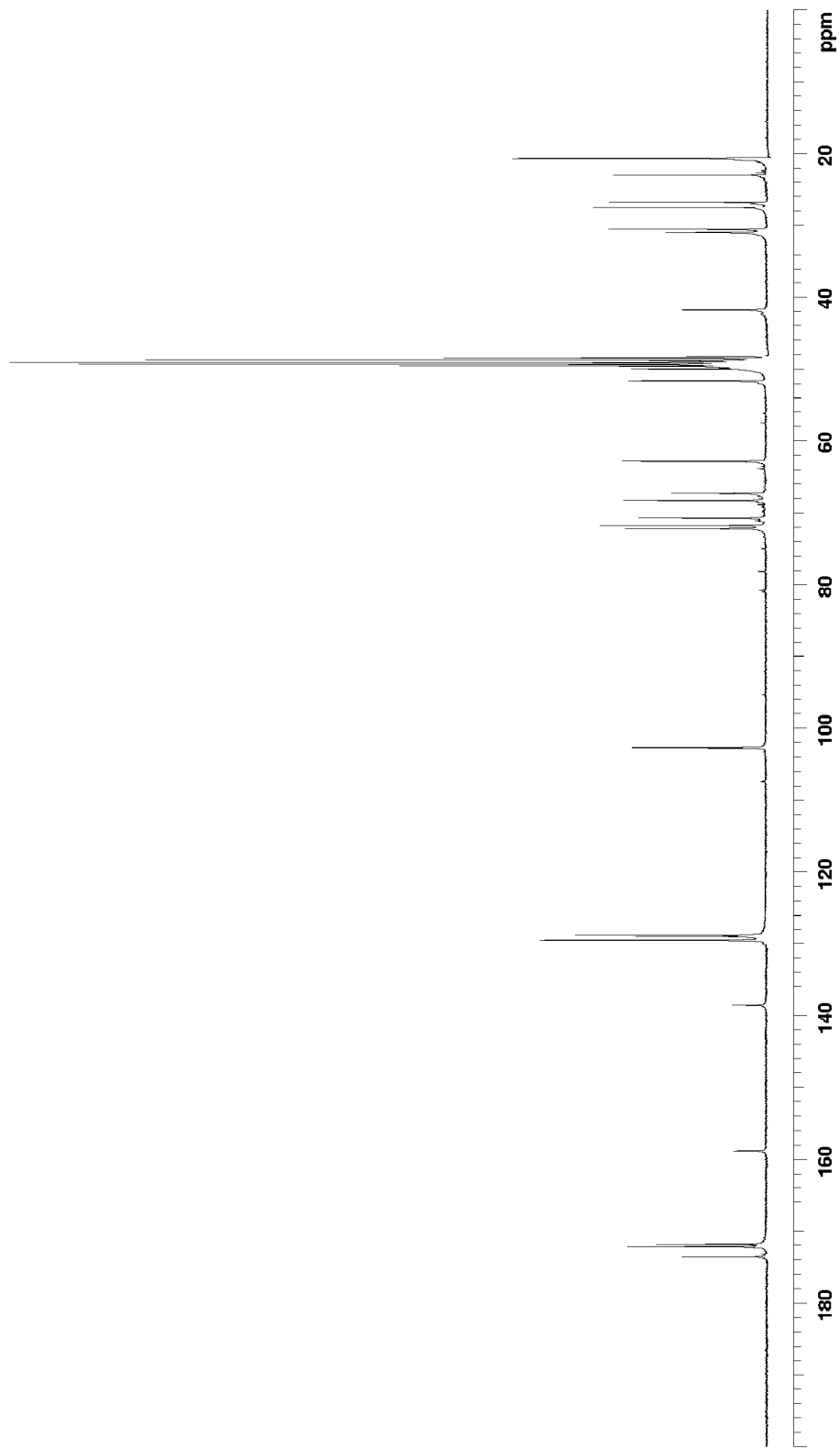
FIG. 8D is a $^{13}$C NMR (CD$_3$OD) spectrum of Compound 8 and provides analysis data of Compound 8 according to an embodiment of the present invention.

Analysis data of Compound 8 is as shown in FIG. 8A and FIG. 8B.

IR (KBr) v 3318 and 1543 (NH), 1748 and 1668 (CO) cm$^{-1}$. $^1$H NMR (CDCl$_3$) δ 7.35 (m, 5 H, Ph), 5.94 (d, J=8.4 Hz, NH), 5.33 (d, J=3.0 H2, H$_4$), 5.26 (dd, J=11.3 and 3.2 Hz, 1 H, H$_3$), 5.11 (AB, J=12.3 Hz, 2 H, CH$_2$Ph), 4.90 (br, 1 H, NH), 4.65 (d, J=8.4 Hz, 1 H, H$_1$), 4.12 (m, 2 H, H$_6$), 4.02-3.81 (m, 3 H, H$_2$, H$_5$, and OCH$_2$CH$_2$), 3.48 (m, 1 H, OCH$_2$CH$_2$), 3.21 (m, 2 H, CH$_2$N), 2.13 (s, 3 H, CH$_3$), 2.05 (s, 3 H, CH$_3$), 2.0 (s, 3 H, CH$_3$), 1.94 (s 3 H, CH$_3$), 1.51 (m, 4 H, OCH$_2$CH$_2$CH$_2$CH$_2$), 1.34 (m, 4 H, OCH$_2$CH$_2$CH$_2$CH$_2$). $^{13}$C NMR (CDCl$_3$) δ 170.44 and 156.56 (CO), 136.64, 128.49, 128.04 and 127.84 (Ph), 100.73 (C$_1$), 70.51, (C$_5$), 69.36 (C$_4$), 69.34 (C$_3$), 66.79 (CH$_2$Ph), 66.53 (OCH$_2$CH$_2$), 61.44 (C$_6$), 51.54 (C$_2$), 40.55 (CH$_2$NH), 29.70 (OCH$_2$CH$_2$), 28.93 (NHCH$_2$CH$_2$), 25.89 (OCH$_2$CH$_2$CH$_2$), 25.07 (CH$_2$CH$_2$CH$_2$N), 23.35 (CH$_3$CONH), 20.67 (CH$_3$COO). $^1$H NMR (CD$_3$OD) δ 7.34 (m, 5 H, Ph), 5.32 (d, J=3.3 Hz, 1 H, H$_4$), 5.05 (m, 3 H, H$_3$ and CH$_2$Ph), 4.54 (d, J=8.4 Hz, 1 H, H$_1$), 4.15-3.95 (m, 4 H, H$_2$, H$_5$ and H$_6$), 3.83 (m, 1 H, OCH$_2$), 3.48 (m, 1 H, OCH$_2$), 3.10 (t, J=6.9 Hz, 2 H, CH$_2$N), 2.13 (s 3 H, CH$_3$), 2.01 (s, 3 H, CH$_3$), 1.94 (s, 3 H, CH$_3$), 1.91 (s, 3 H, CH$_3$), 1.51 (m, 4 H, OCH$_2$CH$_2$CH$_2$CH$_2$CH$_2$), 1.34 (m, 4 H, OCH$_2$CH$_2$CH$_2$CH$_2$). $^{13}$C NMR (CD$_3$OD) δ 173.52, 172.13 and 171.11 (CO), 158.88, 138.55, 129.49 and 128.96 and 128.74 (Ph), 102.66 (C$_1$), 72.17 (C$_5$), 71.76 (C$_4$), 70.70 (C$_3$), 68.25 (CH$_2$Ph), 67.27 (OCH$_2$CH$_2$), 62.79 (C$_6$), 51.69 (C$_2$), 41.73 (CH$_2$N), 30.89 (OCH$_2$CH$_2$), 30.51 (NHCH$_2$CH$_2$), 27.45 (OCH$_2$CH$_2$CH$_2$), 26.68 (CH$_2$CH$_2$CH$_2$N), 22.93 (CH$_3$), 20.65 (CH$_3$). MS m/z 521 (M$^+$-CH$_3$).

IX. Synthesis of Compound 9 (6'-Aminohexyl 2-acetamio-3,4,6-tri-O-acetyl-2-deoxy-β-D-galactopyranoside (ah-GalNAc$_4$))

Compound 8 (0.66 g, 1.14 mmol) was dissolved in ethanol (20 mL), then 10% Pd/C (0.08 g) was added, and the mixture was placed in a hydrogenation unit, and shaken under a hydrogen atmosphere of 50 psi for about 15-24 h, and then filtered. A filtrate was dried by evaporation under vacuum, to obtain Compound 9 (ah-GalNAc$_4$) (0.51 g, 100%).

Figure 9B:
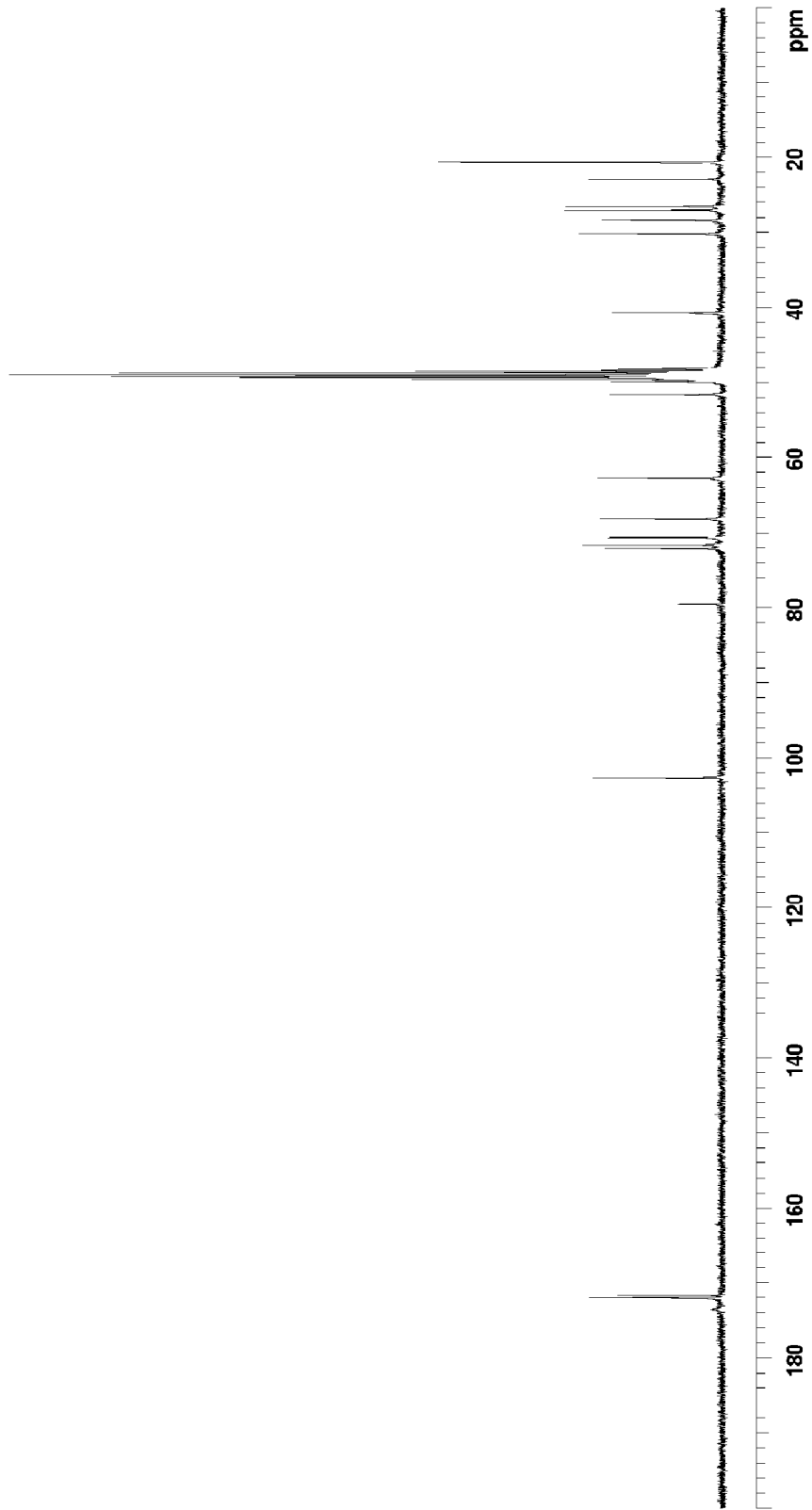
FIG. 9B is a $^{13}$C NMR (CD$_3$OD) spectrum of Compound 9 and provides analysis data of Compound 9 according to an embodiment of the present invention.

Analysis data of Compound 9 (ah-GalNAc$_4$) is as shown in FIG. 9A and FIG. 9B.

IR (neat) v 3256 and 3377 (NH$_2$), 1747 and 1657 (CO) cm$^{-1}$. $^1$H NMR (CD$_3$OD) δ 5.33 (d, J=2.7 Hz, 1 H, H$_4$), 5.05 (dd, J=11.4 and 3.3 Hz, 1 H, H$_3$), 4.55 (d, J=8.4 Hz, 1 H, H$_1$), 4.18-3.97 (m, 4 H, H$_2$, H$_5$ and H$_6$), 3.86 (m, 1 H, OCH$_2$), 3.52 (m, 1 H, OCH$_2$), 2.92 (t, J=7.5 Hz, 2 H, CH$_2$N), 2.14 (s, 3 H, CH$_3$), 2.02 (s, 3 H, CH$_3$), 1.94 (s, 3 H, CH$_3$), 1.93 (s, 3 H, CH$_3$), 1.46 (m, 4 H, OCH$_2$CH$_2$CH$_2$CH$_2$CH$_2$), 1.42 (m, 4 H, OCH$_2$CH$_2$CH$_2$CH$_2$). $^{13}$C NMR (CD$_3$OD) δ 172.03, 171.97 and 171.61 (CO), 102.66 (C$_1$), 72.12 (C$_5$), 71.76 (C$_4$), 70.64 (C$_3$), 68.17 (OCH$_2$), 67.72 (C$_6$), 51.52 (C$_2$), 40.75 (CH$_2$N), 30.19 (OCH$_2$CH$_2$), 28.36 (CH$_2$CH$_2$N), 27.02 (OCH$_2$CH$_2$CH$_2$), 26.35 (CH$_2$CH$_2$CH$_2$N), 22.95 (CH$_3$), 20.58 (CH$_3$). MS m/z 446 (M$^+$), 387 (M$^+$-CH$_3$COO).

X. Synthesis of Compound 10 (6-[3',6'-Diaza-5'-oxo-3'-(2"-triphenylmethylthioethyl)-8'-triphenylmethylthio]octanamidohexyl β-N-acetylgalactoseamine per-o-acetate)

Compound 5 (1.93 g, 2.63 mmol), Compound 9 (1.18 g, 2.63 mmol), triethylamine (1.84 mL, 13.2 mmol), 1,3-dicyclohexylcarbodiimide (1.63 g, 7.88 mmol), and N-hydroxysuccinimide (0.45 g, 3.94 mmol) were added to chloroform (80 mL) in a 250 mL round bottom flask, and heated to reflux for 48 h. After cooling, the solution was washed with an aqueous NaHCO$_3$ solution (2×50 mL). An organic phase was dried over anhydrous sodium sulfate, concentrated under vacumm, and then separated and purified through LC (SiO$_2$, CHCl$_3$:CH$_3$OH=95:5), to obtain Compound 10 (1.79 g, 58%).

Figure 10A:
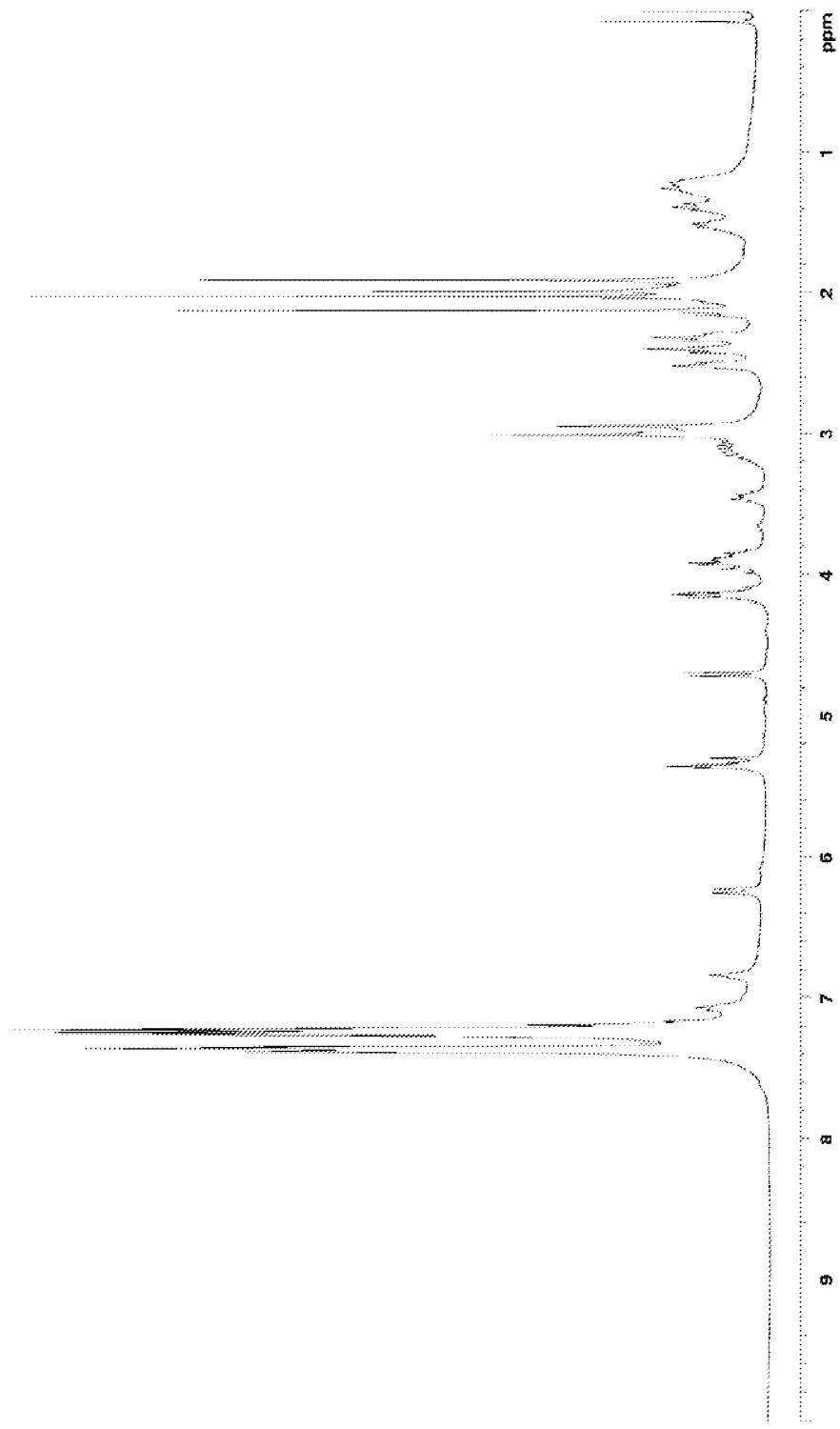
FIG. 10A is a $^1$H NMR (CDCl$_3$) spectrum of Compound 10 and provides analysis data of Compound 10 according to an embodiment of the present invention.
Figure 10B:
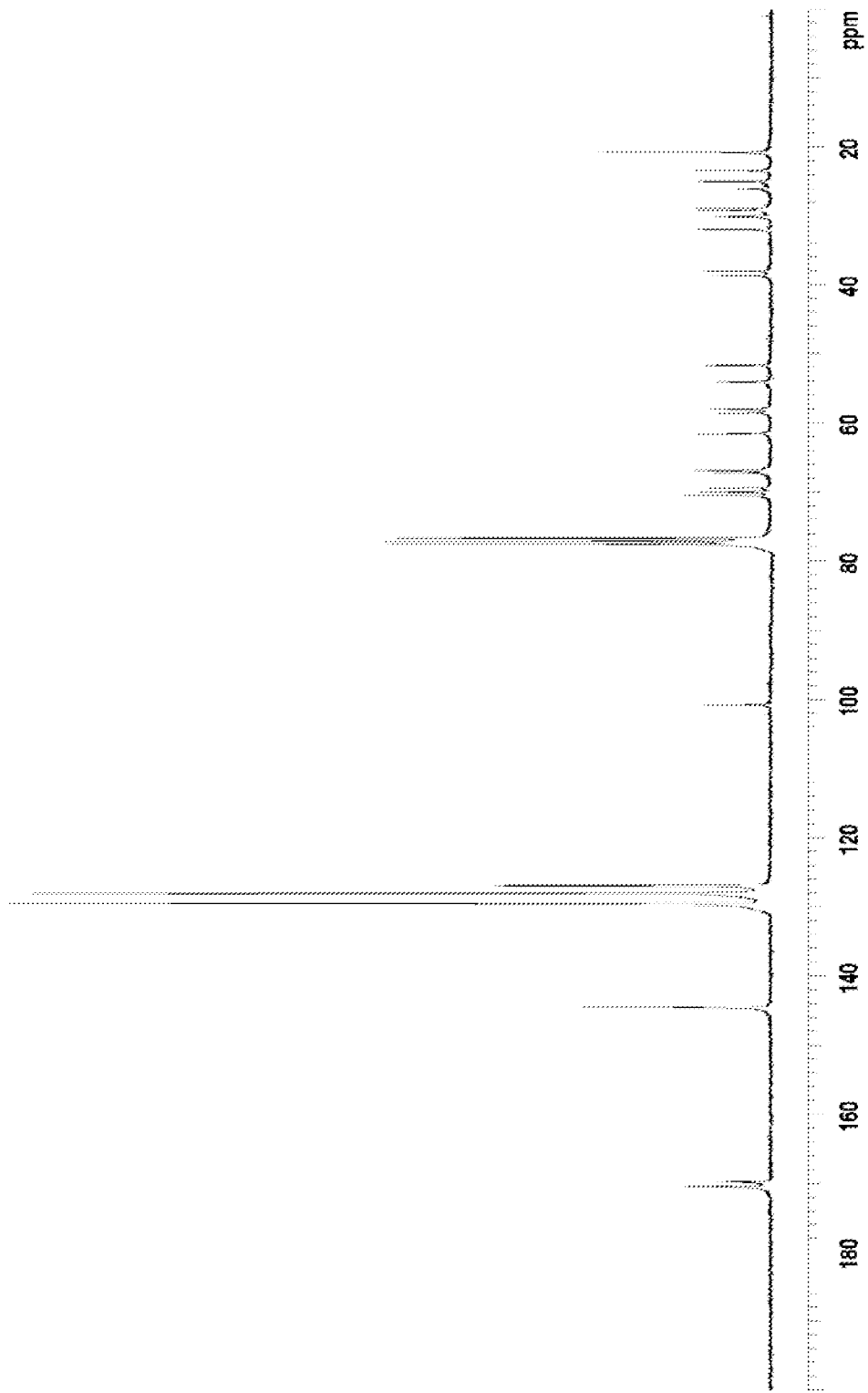
FIG. 10B is a $^{13}$C NMR (CDCl$_3$) spectrum of Compound 10 and provides analysis data of Compound 10 according to an embodiment of the present invention.

Analysis data of Compound 10 is as shown in FIG. 10A and FIG. 10B.

IR (neat) v 3287 and 2929 and 1538 (NH), 1748 and 1658 (CO) cm$^{-1}$. $^1$H NMR (CDCl$_3$) δ7.38 (m, 3 H, Ph), 7.21 (m, 12H, Ph), 7.07 (NH), 6.84 (NH), 6.25 (d, J=8.4 Hz, NH), 5.36 (d, J=2.4 Hz, H$_4$), 5.36 (dd, J=17.4 Hz, 1 H, H$_3$), 4.72 (d, J=8.4 Hz, 1 H, H$_1$), 4.15 (m, 2 H, H$_6$), 4.00-3.80 (m, 3 H, H$_2$, H$_5$, and OCH$_2$CH$_2$), 3.45 (m, 1 H, OCH$_2$CH$_2$), 3.15 (m, 2 H, CH$_2$N), 3.00 (s, 2 H, CH$_2$CO), 2.95 (m, 4 H, CH$_2$CO and CH$_2$NH), 2.52 (t, J=6.3 Hz, 2 H, CH$_2$N), 2.41 (t, J=6.3 Hz, CH$_2$S), 2.32 (t, J=6.0 Hz, CH$_2$S). 2.03 (s, 3 H, CH$_3$), 1.99 (s, 3 H, CH$_3$), 1.95 (s, 3 H, CH$_3$), 1.94 (s 3 H, CH$_3$), 1.40 (m, 4 H, OCH$_2$CH$_2$CH$_2$CH$_2$CH$_2$), 1.22 (m, 4 H, OCH$_2$CH$_2$CH$_2$CH$_2$). $^{13}$C NMR (CDCl$_3$) δ 170.51 and 170.45 and 170.42 and 170.35 and 169.82 and 169.65 (CO), 144.53, 144.45, 129.51, 129.45, 128.04, 127.99, 126.96 and 126.85 (Ph), 100.73 (C$_1$), 70.53, (C$_5$), 70.01 (C$_4$), 69.37 (C$_3$), 67.18 (OCH$_2$CH$_2$), 66.95 and 66.86 (CPh$_3$), 61.51, 58.54 and 57.99 (CH$_2$), 54.05 (C$_6$), 51.63 (C$_2$), 38.64 and 38.05 (CH$_2$NH), 32.04 and 30.18 (CH$_2$S). 29.21 (OCH$_2$CH$_2$), 28.93 (NHCH$_2$CH$_2$), 26.08 (OCH$_2$CH$_2$CH$_2$), 24.95 (CH$_2$CH$_2$CH$_2$N), 23.40 (CH$_3$CONH), 20.72 (CH$_3$COO).

XI. Synthesis of final product (6-[3',6'-Diaza-5'-oxo-3'-(2"-triphenylmethyl thioethyl)-8'-triphenylmethylthio]octanamidohexyl β-N-acetylgalactosamine) (OCTAM-ah-GalNAc)

Compound 10 (1.79 g, 1.54 mmol) was added and dissolved in anhydrous methanol (30 mL), and then sodium methylate solution Natrium methylat-Losung (0.5 M $CH_3ONa/CH_3OH$) (0.6 mL) was added, and stirred at room temperature for 30 min. In an ice bath, 0.1N HCl solution was slowly added dropwise, to adjust PH value to be 6, and then the solution was concentrated under vacuum, and a residue was separated and purified through LC ($SiO_2$, $CHCl_3$: $CH_3OH$=90:10), to obtain the product CTAM-ah-GalNAc (1.30 g, 81%).

Figure 11A:
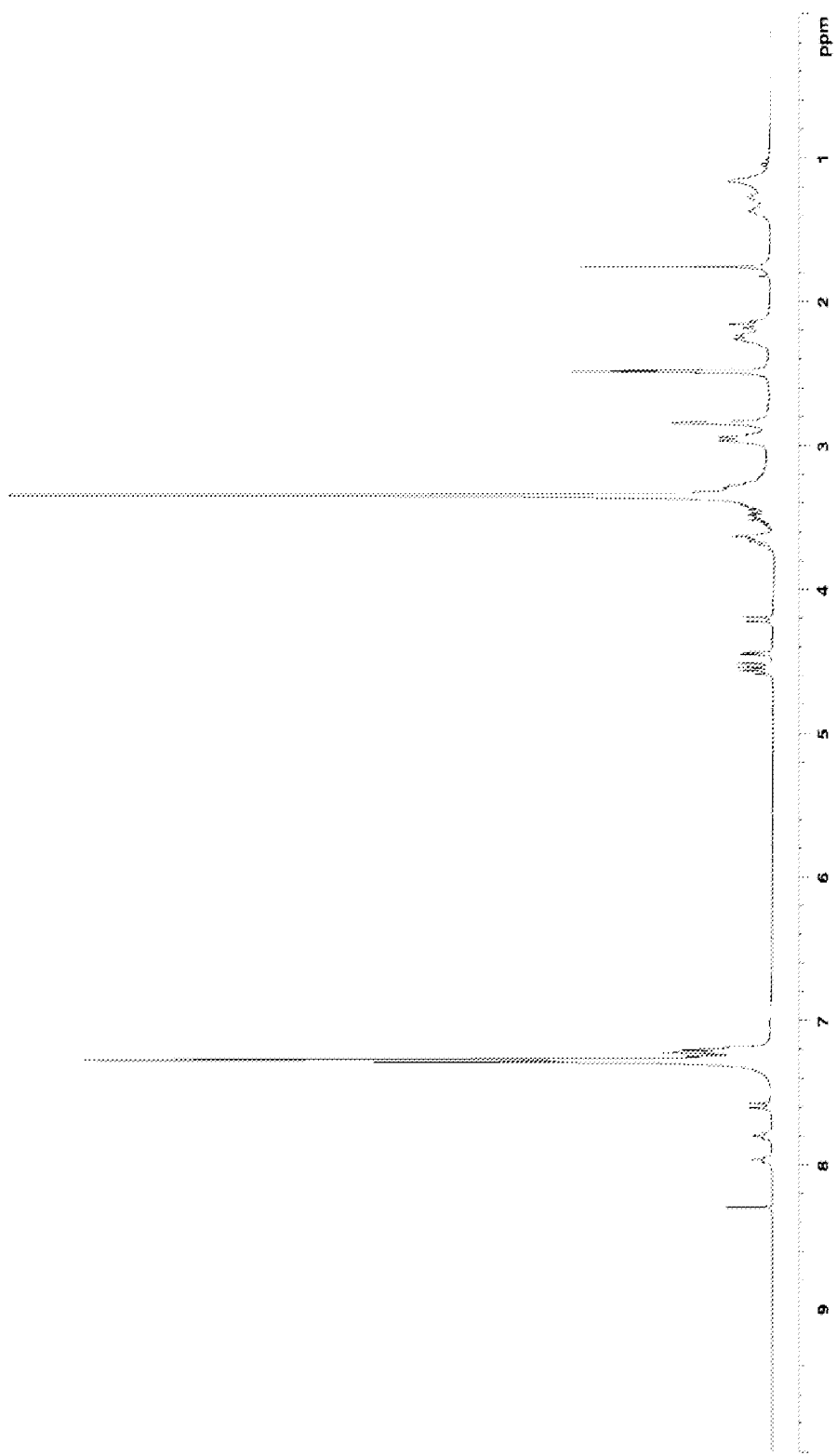
FIG. 11A is a 1H NMR (DMSO) spectrum of Compound 11 and provides analysis data of Compound 11 according to an embodiment of the present invention.
Figure 11B:
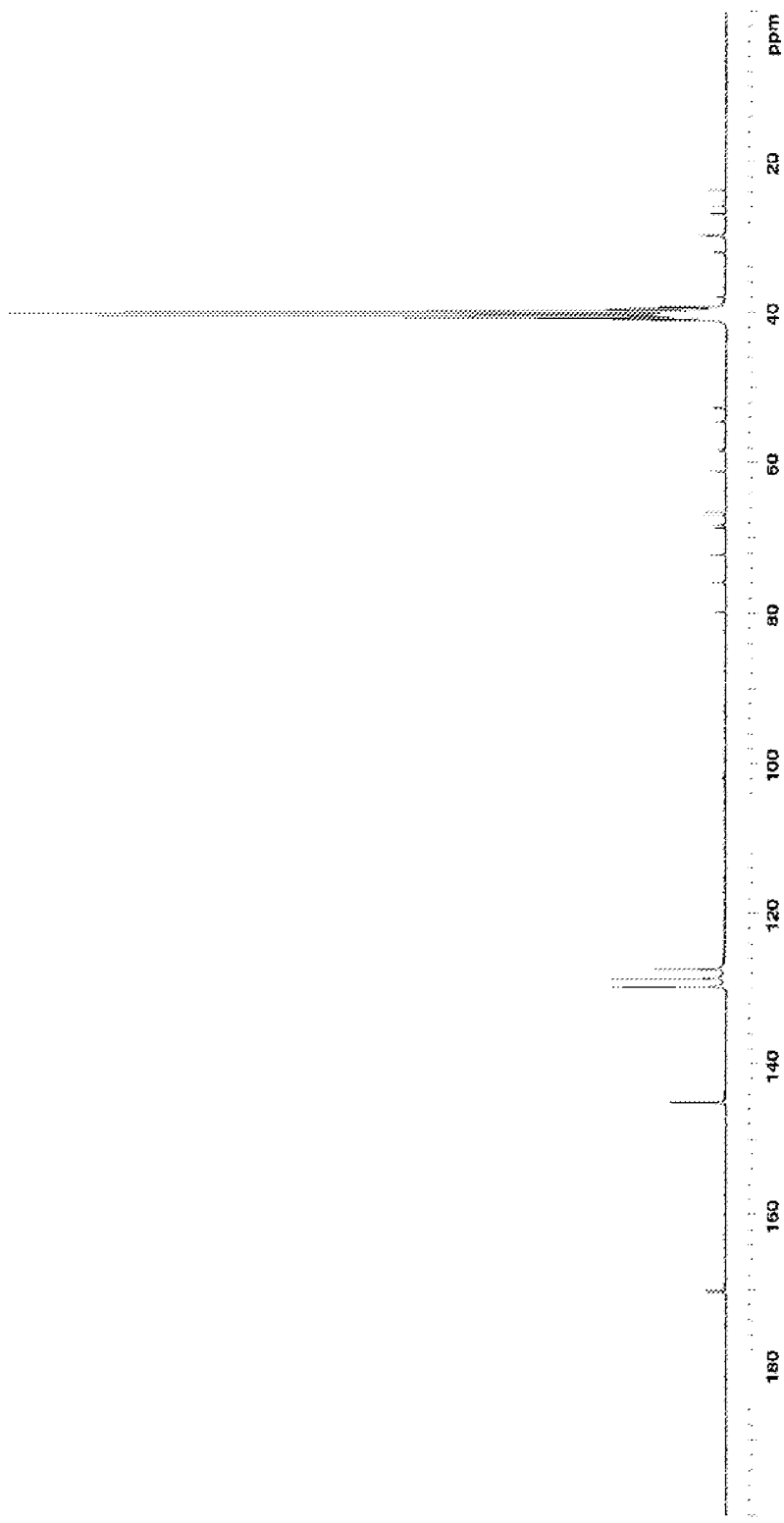
FIG. 11B is a $^{13}$C NMR (DMSO) spectrum of Compound 11 and provides analysis data of Compound 11 according to an embodiment of the present invention.

Analysis data of compound OCTAM-ah-GalNAc is as shown in FIG. 11A and FIG. 11B.

IR (neat) v 3300 (OH), 2930 and 1539 (NH), 160 (CO) $cm^{-1}$. $^1H$ NMR (DMSO) 7.95 (NH), 7.80 (NH), 7.60 (d, J=6 Hz, NH), 67.35 (m, 3 H, Ph), 7.21 (m, 12 H, Ph), 4.58 (d, J=2.6 Hz, $H_4$), 4.50 (dd, J=15 Hz, 1 H, $H_3$), 4.45 (d, J=8.0 Hz, 1 H, $H_1$), 4.20 (d, 2 H, $H_6$), 3.70-3.60 (m, 3 H, $H_2$, $H_5$, and $OCH_2CH_2$), 3.48 (m, 1 H, $OCH_2CH_2$), 2.95 (m, 4 H, $CH_2CO$ and $CH_2NH$), 2.85 (t, J=6.2 Hz, 2 H, $CH_2N$), 2.25 (t, J=6.3 Hz, $CH_2S$), 2.18 (t, J=6.0 Hz, $CH_2S$). 1.76 (s, 3 H, $CH_3$), 1.38-1.22 (m, 4 H, $OCH_2CH_2CH_2CH_2CH_2$), 1.16 (m, 4 H, $OCH_2CH_2CH_2CH_2$). $^{13}C$ NMR (DMSO) δ 170.43 and 170.22 and 170.03 (CO), 145.15, 145.08, 129.77, 129.73, 128.70, 127.41 (Ph), 102.03 ($C_1$), 79.85, ($C_5$), 75.92 ($C_4$), 72.22 ($C_3$), 68.67 ($OCH_2CH_2$), 68.21 ($OCH_2CH_2$), 61.14, 58.51 and 58.18 ($CH_2$), 54.49 ($C_6$), 52.78 ($C_2$), 38.89 and 37.97 ($CH_2NH$), 32.04 and 29.82 ($CH_2S$). 29.75 ($OCH_2CH_2CH_2$), 26.86 ($CH_2CH_2CH_2N$), 25.80 ($CH_3CONH$), 23.76 ($CH_3COO$).

Other Embodiments

All features disclosed in the specification can be combined in any manner, and each feature can be replaced by the same, equivalent, or similar alternative features. Therefore, unless specified otherwise, each feature disclosed herein is merely an example of a wide series of the same or similar features. Based on the description, necessary features of the present invention can be easily recognized persons skilled in the art, and various alternations and modifications for various uses or conditions can be achieved, without departing from the spirit and scope of the present invention. The modifications and substitutions to the reagents such as the reactants, the thiol protecting group, and the reducing agents, and to the materials and equipments used in filtration under vacuum and LC as disclosed in the embodiments can be implemented by persons of ordinary skill in the art, without departing from the innovative spirit and scope of the present invention. Therefore, the present invention is not limited to the invention as claimed in the accompanying claims and equivalents thereof. Therefore, other embodiments are also within the scope of the accompanying claims.

All the patents and publications mentioned in the specification indicate the knowledge degree of persons of ordinary skill in the art. All the patents and publications mentioned in the specification are incorporated herein by reference in their entirety, and each patent or publication should be construed to be independently incorporated herein by reference in its entirety clearly.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A bifunctional compound with a monosaccharide and a $N_2S_2$ ligand, having the following structure:

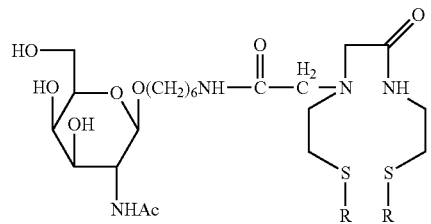

wherein, R is hydrogen or a thiol protecting group.

2. The bifunctional compound according to claim 1, wherein the thiol protecting group is selected from a group consisting of phenylcarbonyl ($COC_6H_5$) and methoxybenzyl ($CH_2C_6H_4OCH_3$).

3. A pharmaceutical composition, comprising:
   the bifunctional compound according to claim 1; and
   an adduct, being a radionuclide or a targeting agent, or a combination thereof.

4. The pharmaceutical composition according to claim 3, wherein the radionuclide is selected from technetium (Tc), rhenium (Re), indium (In), and a combination thereof.

5. The pharmaceutical composition according to claim 4, wherein a compound of technetium (Tc), rhenium (Re), and indium (In) is an oxide.

6. The pharmaceutical composition according to claim 3, wherein the targeting agent is a peptide or a protein.

7. A bifunctional compound with a monosaccharide and a $N_2S_2$ ligand, having the following structure:

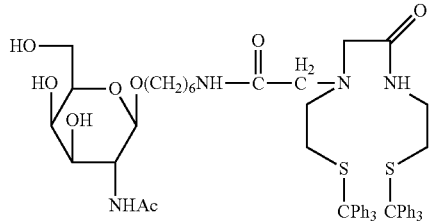

8. A pharmaceutical composition, comprising:
   the bifunctional compound according to claim 7; and
   an adduct, being a radionuclide or a targeting agent, or a combination thereof.

9. The pharmaceutical composition according to claim 8, wherein the radionuclide is selected from technetium (Tc), rhenium (Re), indium (In), and a combination thereof.

10. The pharmaceutical composition according to claim 9, wherein a compound of technetium (Tc), rhenium (Re), and indium (In) is an oxide.

11. The pharmaceutical composition according to claim 8, wherein the targeting agent is a peptide or a protein.

* * * * *